(12) United States Patent
Ameri et al.

(10) Patent No.: US 9,573,717 B2
(45) Date of Patent: Feb. 21, 2017

(54) STABLE THERAPEUTIC FORMULATIONS

(71) Applicant: ALZA CORPORATION, Vacaville, CA (US)

(72) Inventors: Mahmoud Ameri, Fremont, CA (US); Michel J. N. Cormier, Mountain View, CA (US); Scott Sellers, San Mateo, CA (US); Yuh-Fun Maa, Millbrae, CA (US)

(73) Assignee: ALZA CORPORATION, Mountain View, CA (US)

( * ) Notice: Subject to any disclaimer, the term of this patent is extended or adjusted under 35 U.S.C. 154(b) by 210 days.

(21) Appl. No.: 14/160,326

(22) Filed: Jan. 21, 2014

(65) Prior Publication Data

US 2014/0260096 A1    Sep. 18, 2014

Related U.S. Application Data

(63) Continuation of application No. 11/617,639, filed on Dec. 28, 2006, now Pat. No. 8,632,801.
(Continued)

(51) Int. Cl.
| | | |
|---|---|---|
| A61K 38/00 | (2006.01) | |
| A61K 9/00 | (2006.01) | |
| B65B 55/00 | (2006.01) | |
| A61K 31/716 | (2006.01) | |
| A61K 38/22 | (2006.01) | |
| A61K 38/29 | (2006.01) | |
| A61M 37/00 | (2006.01) | |
| B65B 31/00 | (2006.01) | |

(Continued)

(52) U.S. Cl.
CPC ............. *B65B 55/00* (2013.01); *A61K 9/0021* (2013.01); *A61K 31/716* (2013.01); *A61K 38/2242* (2013.01); *A61K 38/29* (2013.01); *A61M 37/0015* (2013.01); *B65B 31/00* (2013.01); *A61K 48/00* (2013.01); *A61K 2039/54* (2013.01); *A61M 2037/0023* (2013.01)

(58) Field of Classification Search
CPC ..... B65B 55/00; A61K 9/0021; A61K 31/655; A61K 38/2013; A61K 38/204; A61K 38/2053; A61K 38/217
See application file for complete search history.

(56) References Cited

U.S. PATENT DOCUMENTS 6,905,016 B2 * 6/2005 Kanios .................. A61F 15/001
                                                                206/204
7,537,795 B2 * 5/2009 Cormier ................ A61K 9/0021
                                                                427/2.28

(Continued)

*Primary Examiner* — Cherie M Stanfield
(74) *Attorney, Agent, or Firm* — Mayer Brown LLP

(57) ABSTRACT

Compositions of and methods for formulating and delivering biologically active agent formulations having enhanced physical stability, and wherein deterioration from the presence of oxygen and/or water is minimized and/or controlled, to yield a stable formulation. The compositions of and methods for formulating and delivering biologically active agents of the present invention further facilitate their incorporation into a biocompatible coating which can be employed to coat a stratum-corneum piercing microprojection, or a plurality of stratum-corneum piercing microprojections of a delivery device, for delivery of the biocompatible coating through the skin of a subject, thus providing an effective means of delivering the biologically active agents.

11 Claims, 13 Drawing Sheets

Related U.S. Application Data

(60) Provisional application No. 60/754,948, filed on Dec. 28, 2005.

(51) Int. Cl.
*A61K 48/00* (2006.01)
*A61K 39/00* (2006.01)

(56) References Cited

U.S. PATENT DOCUMENTS

| | | | | |
|---|---|---|---|---|
| 8,361,022 B2* | 1/2013 | Ameri | ............... | A61K 9/0021 |
| | | | | 424/449 |
| 8,632,801 B2* | 1/2014 | Ameri | ............... | A61K 9/0021 |
| | | | | 424/234.1 |
| 8,920,817 B2* | 12/2014 | Ameri | ............... | A61K 9/0021 |
| | | | | 424/400 |
| 2002/0128599 A1* | 9/2002 | Cormier | ............... | A61K 9/0021 |
| | | | | 604/116 |
| 2002/0168401 A1* | 11/2002 | Kanios | ............... | A61F 15/001 |
| | | | | 424/449 |
| 2004/0265354 A1* | 12/2004 | Ameri | ............... | A61K 9/0021 |
| | | | | 424/423 |
| 2006/0275170 A1* | 12/2006 | Ameri | ............... | A61K 9/0021 |
| | | | | 422/22 |
| 2007/0184096 A1* | 8/2007 | Ameri | ............... | A61K 9/0021 |
| | | | | 424/449 |

* cited by examiner

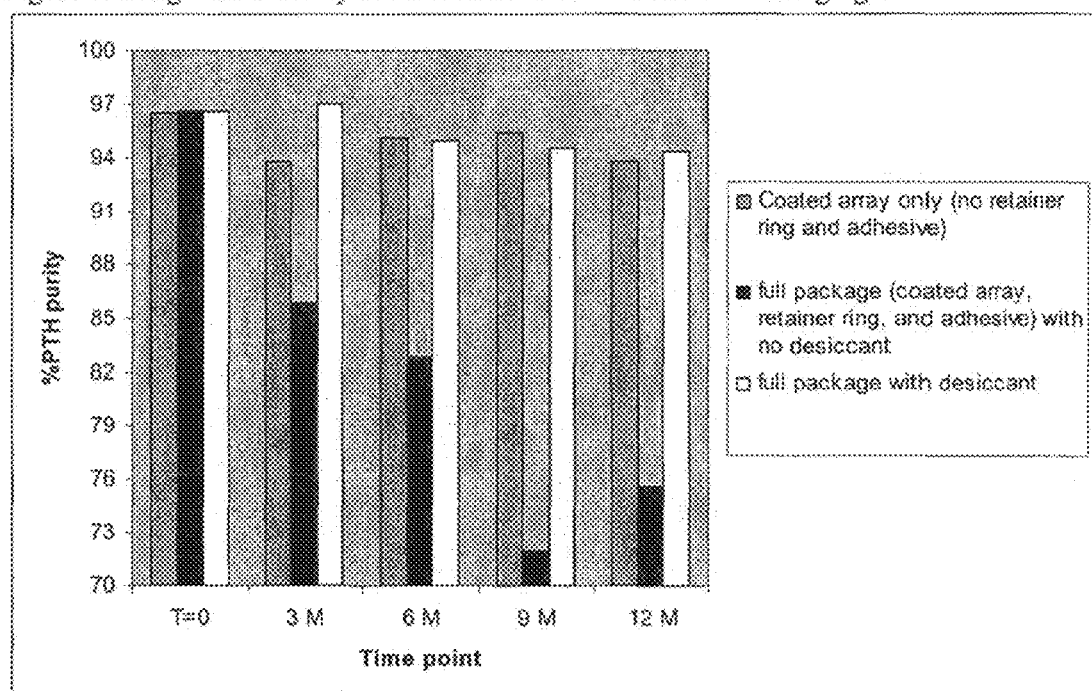
Figure 7: Long-term Stability of Macroflux® PTH in Different Packaging Conditions

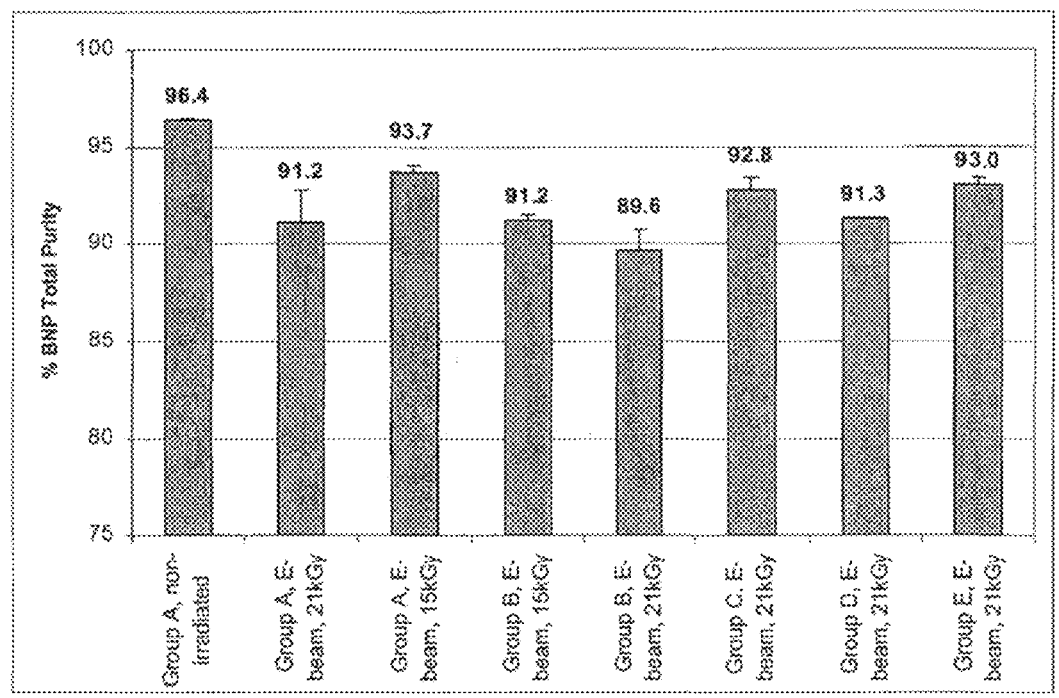
Figure 8. % BNP Purity by HPLC following e-beam Treatment (T=0)
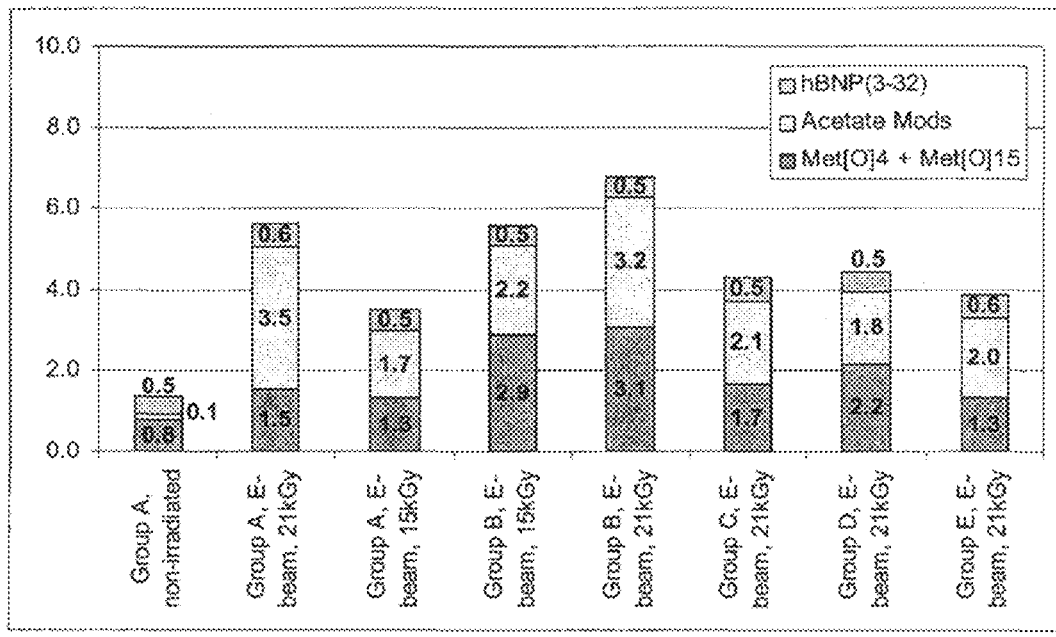
Figure 9. BNP Degradation Profile by HPLC at T=0

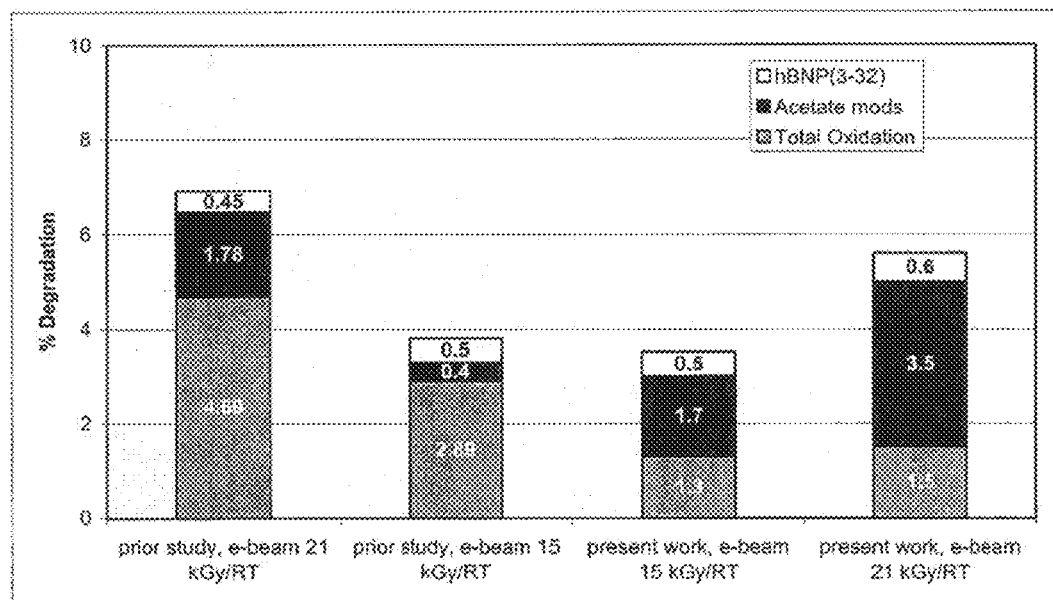
Figure 10. Comparison of E-beam Treatment Degradation Profiles from Previous and Current Studies.
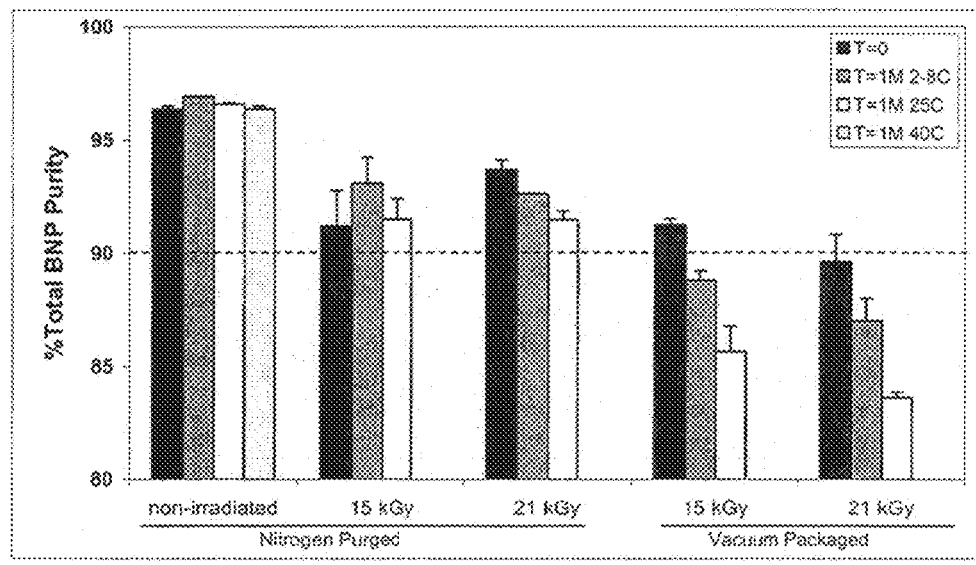
Figure 11. 1M Stability Data following E-Beam Treatment

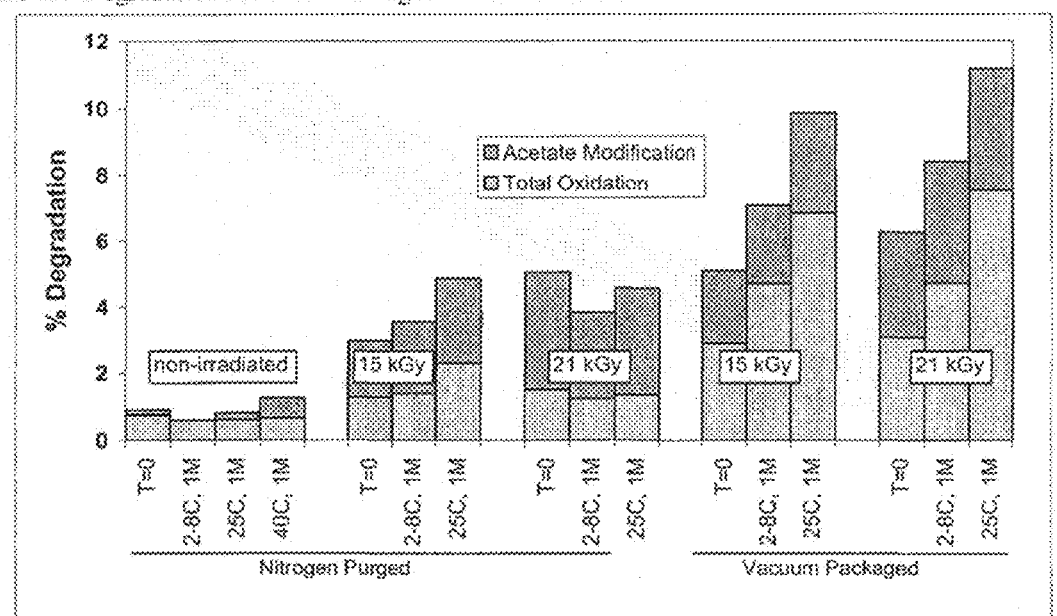
Figure 12. Degradation Profile following E-Beam Treatment

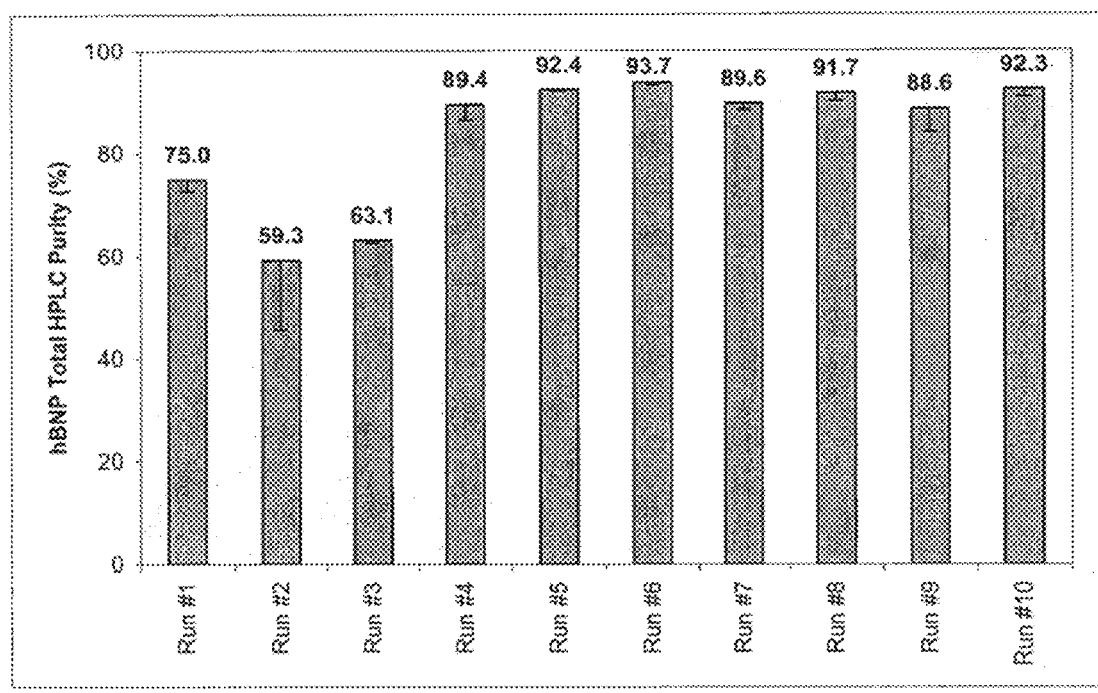
Figure 13. Total hBNP % Peak Area Purity (T=0)

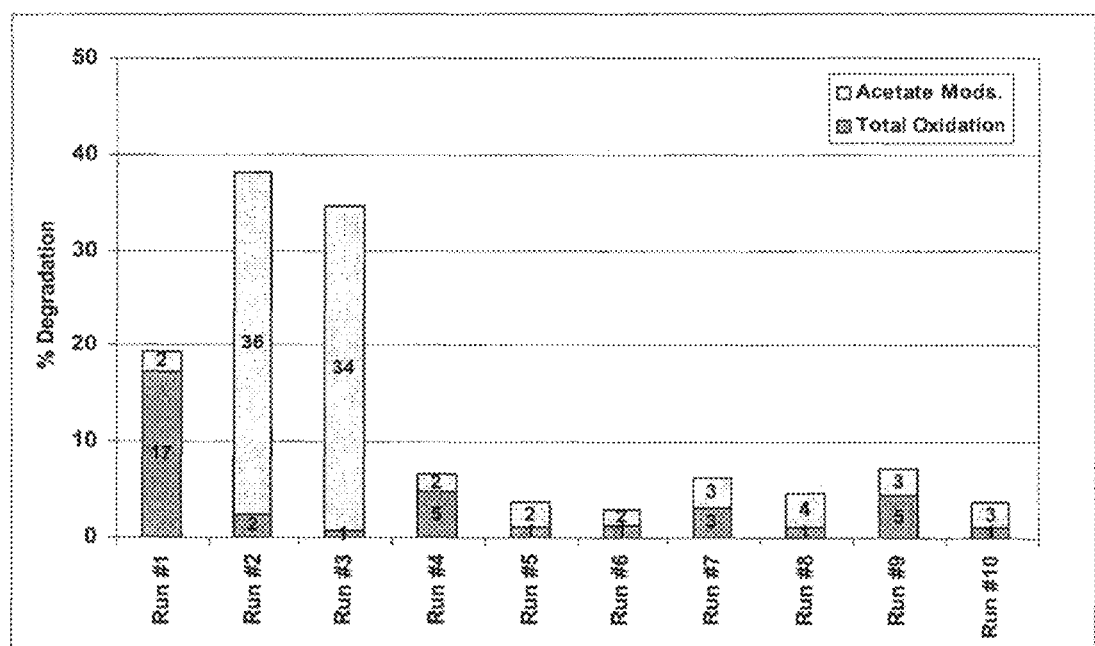
Figure 14. HPLC Degradation Profile (T=0)

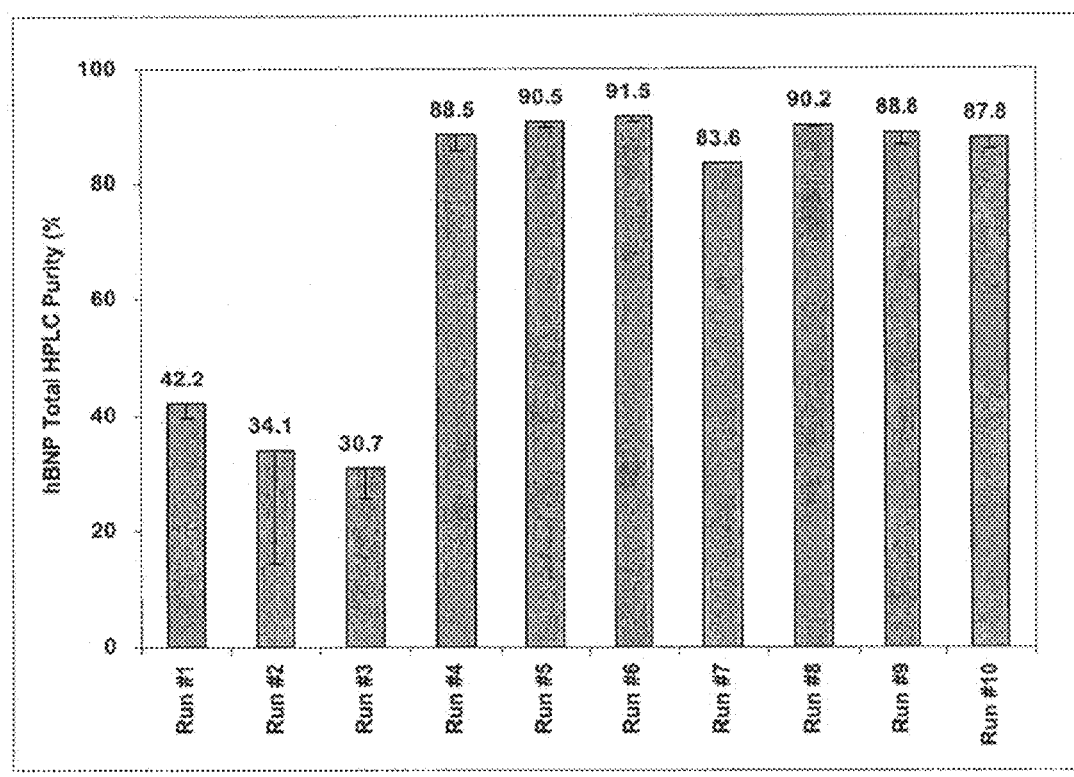
Figure 15. Total hBNP % Peak Area Purity (T=1M, 25C)

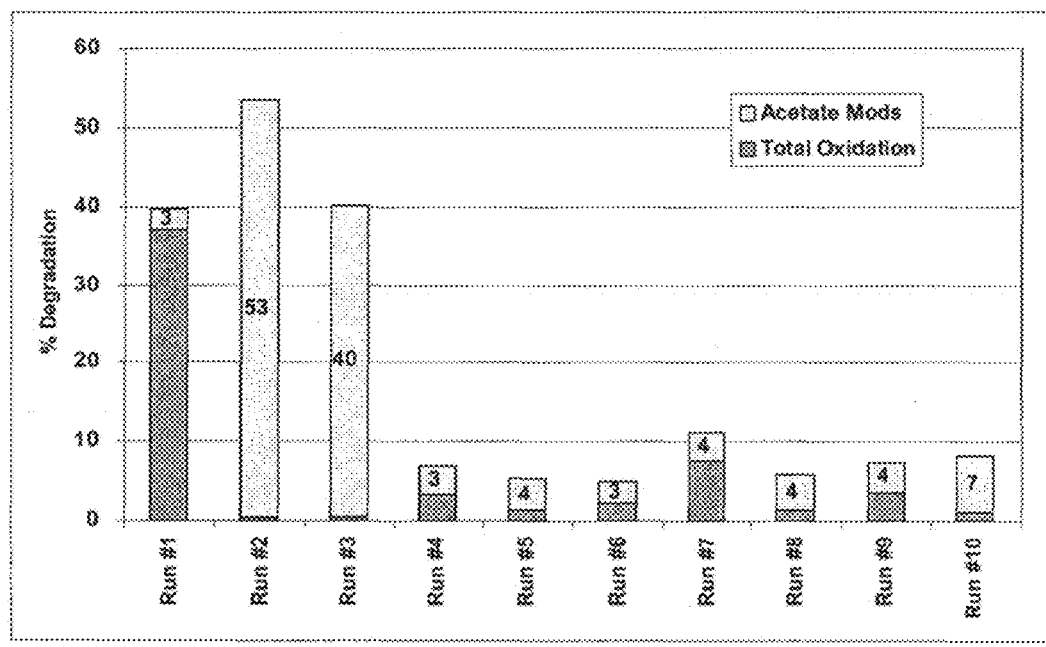
Figure 16. HPLC Degradation Profile (T=1M, 25C)

STABLE THERAPEUTIC FORMULATIONS

RELATED APPLICATIONS

The present application is a continuation of U.S. Ser. No. 11/617,639, filed Dec. 28, 2006, which claims priority from U.S. Provisional Application No. 60/754,948 filed on Dec. 28, 2005, the contents of which are herein incorporated by reference in their entirety.

FIELD OF THE PRESENT INVENTION

The present invention relates generally to biologically active agent compositions and methods for formulating and delivering such compositions. More particularly, the present invention relates to compositions of and methods for formulating and delivering physically stabilized biologically active agent compositions by minimizing the exposure of such biologically active agent compositions to oxygen and water.

BACKGROUND OF THE INVENTION

A great number and variety of biologically active agents are known in the art to have therapeutic benefits when delivered appropriately to a patient having a condition upon which such biologically active agents can exert a beneficial effect. These biologically active agents comprise several broad classes, including, but not limited to peptides or proteins, such as hormones, proteins, antigens, repressors/activators, enzymes, and immunoglulins, among others. Therapeutic applications include treatment of cancer, hypercalcemia, Paget's disease, osteoporosis, diabetes, cardiac conditions, including congestive heart failure, sleep disorders, Chronic Obstructive Pulmonary Disease (COPD) and anabolic conditions, to name a few.

In the art, formulating such biologically active agent formulations in a therapeutically effective and commercially viable manner has been problematic, due in part, to the tendency of many biologically active agents to deteriorate in the presence of oxygen and water. Particularly susceptible to oxidation include the amino acids methionine and cysteine. Water causes degradation of large number of biological agents. This affects particularly peptides and proteins as a result of hydrolysis of the amide bond.

References have been published which discuss the effects of oxidation and hydrolysis on biologically active agents during manufacture and storage. For example, Pikal M J, Dellerman K, Roy M L. Formulation and stability of freeze-dried proteins: effects of moisture and oxygen on the stability of freeze-dried formulations of human growth hormone. Dev Biol Stand. 1992; 74:21-38; Lai, Mei C.; Hageman, Michael J.; Schowen, Richard L.; Borchardt, Ronald T.; Topp, Elizabeth M. Chemical Stability of Peptides in Polymers. 1. Effect of Water on Peptide Deamidation in Poly(vinyl alcohol) and Poly(vinyl pyrrolidone) Matrixes. Journal of Pharmaceutical Sciences (1999), 88(10), 1073-1080, address how biological active agents experience deterioration due to oxidation or hydrolysis when exposed to air or water over extended periods of time.

The deterioration of biologically active agents in formulations is particularly problematic when biologically active agents are administered by transdermal delivery. The word "transdermal", as used herein, is a generic term that refers to delivery of an active agent (e.g., a therapeutic agent, such as a drug, pharmaceutical, peptide, polypeptide or protein) through the skin to the local tissue or systemic circulatory system without substantial cutting or penetration of the skin, such as cutting with a surgical knife or piercing the skin with a hypodermic needle. Transdermal agent delivery includes delivery via passive diffusion as well as delivery based upon external energy sources, such as electricity (e.g., iontophoresis) and ultrasound (e.g., phonophoresis).

Numerous transdermal agent delivery systems and apparatus have been developed that employ tiny skin piercing elements to enhance transdermal agent delivery. Examples of such systems and apparatus are disclosed in U.S. Pat. Nos. 5,879,326, 3,814,097, 5,250,023, 3,964,482, Reissue No. 25,637, and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, WO 98/29365 and US PublicationNos. US2004/0062813, US2004/0265354, US2005/0090009, US2005/0106209, US20050123507, US2005/0226922, US2005/0256045, and US2005/0266011; all incorporated herein by reference in their entirety.

The disclosed systems and apparatus employ piercing elements of various shapes and sizes to pierce the outermost layer (i.e., the stratum corneum) of the skin, and thus enhance the agent flux. The piercing elements generally extend perpendicularly from a thin, flat member, such as a pad or sheet. The piercing elements are typically extremely small, some having a rnicroprojection length of only about 25-400 microns and a microprojection thickness of only about 5-50 microns. These tiny piercing/cutting elements make correspondingly small microslits/microcuts in the stratum corneum for enhanced transdermal agent delivery therethrough. The active agent to be delivered is associated with one or more of the microprojections, usually by coating the rnicroprojections with the formulation or by the use of a reservoir that communicates with the stratum corneum after the microslits are formed.

The current manufacturing and packaging processes, however, are problematic, especially where the microprojections are coated with the formulation by drying the formulation on the microprojections, as described in U.S. patent application Publication No. 2002/0128599. The formulation is usually an aqueous formulation. During the drying process, all volatiles, including water are mostly removed, however, the final solid coating still contains typically about 3% water. The presence of water can lead to deterioration of the biologically active agent in the formulation because of hydrolysis.

The current manufacturing and packaging processes are also problematic because oxygen is present during each phase. While the manufacturing phase is a relatively short period of time, the packaging and storage phase can be quite lengthy. Storage times of transdermal delivery systems are likely to be for lengthy periods of time before they are used (i.e., extended shelf life of several months is not uncommon). The biologically active agents in the coatings, therefore, are subject to oxidation and deterioration. For purposes of this application, reference to the term "package" or "packaging" will be understood to also include reference to "storage" or "storing".

Accordingly, physical stabilization, especially minimizing the exposure of the biologically active agent formulations over time to oxidation and hydrolysis, is an important step in assuring efficacy of the therapeutic agents, particularly when the mode of delivery of the therapeutic agent is via a transdermal delivery device having a plurality of microprojections coated with an agent containing biocompatible coating.

It would therefore be desirable to provide compositions of and methods for formulating and delivering biologically active agents having enhanced physical stability.

It would be further desirable to provide compositions of and methods for formulating and delivering biologically active agents wherein deterioration of the biologically active agent from oxygen and/or water is minimized and/or controlled.

It would be further desirable to provide compositions of and methods for formulating and delivering biologically active agents that exhibit maximal or optimal shelf lives.

SUMMARY OF THE INVENTION

The present invention provides biologically active agents having enhanced physical stability, wherein the biologically active agents are coated on a transdermal delivery device having a plurality of skin-piercing microprojections that are adapted to deliver the agent through the skin of a subject and the device is manufactured and/or packaged in a dry inert atmosphere and/or a partial vacuum.

In accordance with the compositions of and methods for formulating and delivering physically stable biologically active agent formulations of the present invention, it has been found that the manufacture and/or packaging of the formulations in a dry inert atmosphere and/or a partial vacuum, substantially free of oxygen and water, substantially reduces or eliminates undesirable deterioration of the biologically active agent.

The present invention provides compositions of and methods for formulating and delivering biologically active agents wherein deterioration from damaging oxygen and/or water is minimized and/or controlled.

The present invention also provides compositions of and methods for formulating and delivering biologically active agents that have maximal or optimal shelf lives.

The present invention further provides biologically active agents having enhanced physical stability, wherein the biologically active agents are contained in a biocompatible coating that is disposed on a transdermal delivery device having a plurality of skin-piercing microprojections that are adapted to deliver the agent through the skin of a subject.

The present invention also provides compositions of and methods for formulating and delivering biologically active agent formulations wherein the formulations are stabilized during their manufacture and storage by the presence of a dry inert atmosphere and/or a partial vacuum, substantially free of oxygen and/or water.

As well, the present invention provides methods for using a dry inert atmosphere and/or a partial vacuum during manufacture and/or packaging to stabilize biologically active agent formulations.

In one embodiment of the invention, there are provided compositions of and methods for formulating and delivering biologically active agents that exhibit improved or optimal physical stability, and which improved or optimal physical stability enhances shelf life of formulations containing the therapeutic agents. The present invention also provides for compositions of and methods for formulating and delivering biologically active agent formulations that have been incorporated in a biocompatible coating that is coated onto a plurality of stratum corneum-piercing microprojections of a transdermal delivery device, the delivery device exhibiting improved or optimal physical stability.

In one embodiment of the present invention, the compositions of and methods for formulating and delivering biologically active agent formulations are suitable for use with a variety of delivery means (e.g., systemic or local delivery), including oral (bolus), oral (timed or pattern release), infusion, injection, subcutaneous implant, pulmonary, mucosal (oral mucosa, ocular, nasal, rectal, vaginal), passive, active and balistic transdermal delivery. Other local delivery, such as treatment of otitis, skin, scalp, nail fungal, bacterial and viral infections, are also within the scope of the invention.

In a preferred embodiment, the compositions of and methods for formulating and delivering biologically active agents are particularly suitable for transdermal delivery using a rnicroprojection delivery device, wherein the biologically active agents are included in a biocompatible coating that is coated on at least one stratum-corneum piercing microprojection, preferably a plurality of stratum-comeum piercing microprojections of a microprojection delivery device.

In one embodiment, the compositions of and methods for formulating and delivering biologically active agents are particularly suitable for transdermal delivery using a microprojection delivery device, wherein the biologically active agents are included in a biocompatible coating that is manufactured and/or packaged in a dry inert atmosphere, preferably nitrogen or argon.

In one embodiment, the compositions of and methods for formulating and delivering biologically active agents are particularly suitable for transdermal delivery using a microprojection delivery device, wherein the biologically active agents are included in a biocompatible coating that is coated on at least one stratumcomeum piercing microprojection, preferably a plurality of stratum-comeum piercing microprojections of a microprojection delivery device, and manufactured and/or packaged in a dry inert atmosphere, preferably nitrogen and argon.

In one embodiment, the compositions of and methods for formulating and delivering biologically active agents are particularly suitable for transderrnal delivery using a microprojection delivery device, wherein the biologically active agents are included in a biocompatible coating that is manufactured and/or packaged in a dry inert atmosphere, preferably nitrogen or argon, and in the presence of a desiccant or oxygen absorber.

In one embodiment, the compositions of and methods for formulating and delivering biologically active agents are particularly suitable for transderrnal delivery using a microprojection delivery device, wherein the biologically active agents are included in a biocompatible coating that is manufactured and/or packaged in a foil lined chamber having a dry inert atmosphere, preferably nitrogen, and a desiccant or oxygen absorber.

In one embodiment, the compositions of and methods for formulating and delivering biologically active agents are particularly suitable for transdermal delivery using a microprojection delivery device, wherein the biologically active agents are included in a biocompatible coating that is manufactured and/or packaged in a partial vacuum.

In one embodiment, the compositions of and methods for formulating and delivering biologically active agents are particularly suitable for transderrnal delivery using a microprojection delivery device, wherein the biologically active agents are included in a biocompatible coating that is manufactured and/or packaged in a dry inert atmosphere, preferably nitrogen, and a partial vacuum.

In one embodiment, the compositions of and methods for formulating and delivering biologically active agents are particularly suitable for transdermal delivery using a microprojection delivery device, wherein the biologically active agents are included in a biocompatible coating that is manufactured and/or packaged in a foil lined chamber having a dry inert atmosphere, preferably nitrogen, a partial vacuum, and a desiccant or oxygen absorber.

In a preferred embodiment, the biologically active agent comprises IIPTH. A particularly preferred form is liPTH(1-34) and analogs thereof.

In another preferred embodiment, the resultant formulation of stable biologically active agents, is incorporated in a biocompatible coating used to coat at least one stratum-corneum piercing microprojection, preferably a plurality of stratum-corneum piercing microprojections, or an array thereof, or a delivery device. Typically, the coating process is carried out in a series of coating steps, with a drying step between each coating step, as disclosed, for example in U.S. Pat. Pub. No. 2002/0132054, to Trautman et al.; the disclosure of which is incorporated by reference herein. The coated microprojections are packaged in a dry inert atmosphere and/or a partial vacuum.

In accordance with a further embodiment of the invention, an apparatus or device for transdermally delivering the stable biologically active agents comprises a microprojection member that includes a plurality of microprojections that are adapted to pierce through the stratum corneum into the underlying epidermis layer, or epidermis and dermis layers, the microprojection member having a biocompatible coating disposed thereon that includes a formulation containing the stable biologically active agents.

In accordance with one embodiment of the invention, a method for manufacturing biologically active agent formulations comprises the following steps: (i) providing a microprojection member having a plurality of microprojections, (ii) providing a formulation of biologically active agent; (iii) forming a biocompatible coating formulation that includes the formulation of biologically active agent, (iv) coating the microprojection member with the biocompatible coating formulation to form a bio compatible coating; and (v) packaging the biocompatible coating under dry inert atmospheric conditions and/or a partial vacuum. In a preferred embodiment a desiccant is included in the packaging.

In accordance with one embodiment of the invention, a method for delivering biologically active agent formulations comprises the following steps: (i) providing a microprojection member having a plurality of microprojections, (ii) providing a formulation of biologically active agent; (iii) forming a biocompatible coating formulation that includes the formulation of biologically active agent, (iv) coating the microprojection member with the biocompatible coating formulation to form a biocompatible coating; (v) packaging the biocompatible coating under dry inert atmospheric conditions and/or a partial vacuum; and (vi) applying the coated microprojection member to the skin of a subject. In a preferred embodiment a desiccant is included in the packaging.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 7 shows long-term stability of Macroflux® PTH in different Packaging Conditions.

FIG. 8 shows % BNP Purity by HPLC following e-beam Treatment (T=0).

FIG. 9 shows BNP Degradation Profile by HPLC at T=0.

FIG. 10 shows a comparison of E-beam treatment degradation profiles from previous and Current Studies FIG. 11 shows 1M stability data following E-beam treatment.

FIG. 12 shows degradation profile following E-beam treatment.

FIG. 13 shows total hBNP % Peak Area Purity (T=0).

FIG. 14 shows HPLC degradation profile (T=0).

FIG. 15 shows total hBNP % Peak Area Purity (T=IM, 25 C).

FIG. 16 shows HPLC degradation profile (T=1M, 25 C).

DETAILED DESCRIPTION OF THE INVENTION

Figure 1:
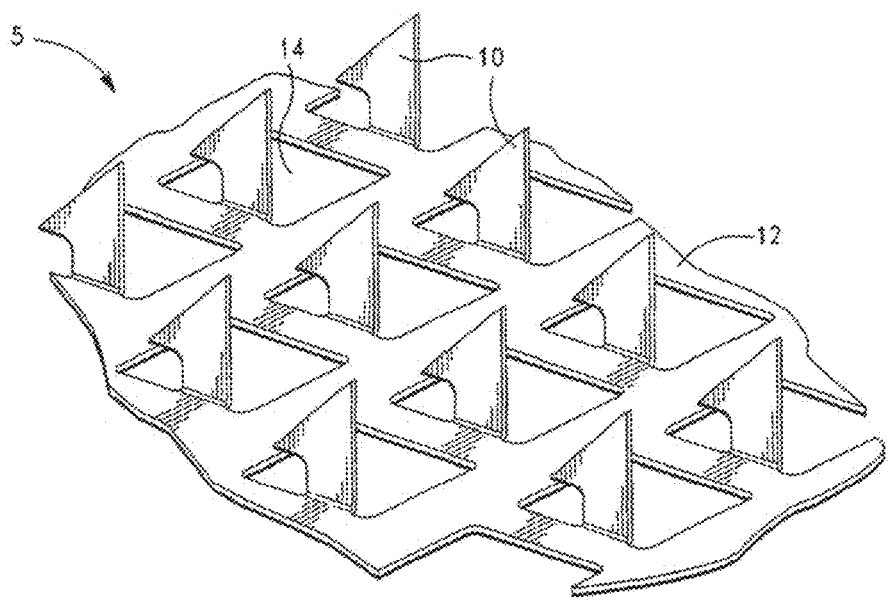
FIG. 1 is a perspective view of a portion of one example of a microprojection array upon which a biocompatible coating having a biologically active agent formulation can be deposited.

Before describing the present invention in detail, it is to be understood that this invention is not limited to particularly exemplified materials, formulations, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "a therapeutic agent" includes two or more such agents; reference to "a microprojection" includes two or more such microprojections and the like.

DEFINITIONS

The term "degradation", as used herein, means the purity of the biological agent decreases from an initial time point.

The terms "desiccant" and "oxygen absorbers" are used interchangeably herein. Unless otherwise clear from the context, the noted terms refer to a agent that absorbs water, usually a chemical agent.

The term "transdermal", as used herein, means the delivery of an agent into and/or through the skin for local or systemic therapy.

The term "deteriorate", as used herein, means that the biologically active agent is diminished or impaired in quality, character, or value.

The term "minimize", as used herein, also means reduce.

The term "transdermal flux", as used herein, means the rate of transdermal delivery.

The term "stable", as used herein to refer to an agent formulation, means the agent formulation is not subject to undue chemical or physical change, including decomposition, breakdown, or inactivation. "Stable" as used herein to refer to a coating also means mechanically stable, i.e. not subject to undue displacement or loss from the surface upon which the coating is deposited.

The terms "therapeutic agent" and "agent", as used herein, mean and include a pharmaceutically active agent and/or a composition of matter or mixture containing an active agent, which is pharmaceutically effective when administered in a therapeutic-effective amount. A specific example of a biologically active active agent is hPTH. It is to be understood that more than one "agent" can be incorporated into the therapeutic agent formulation(s) of the present invention, and that the terms "agent" and "therapeutic agent" do not exclude the use of two or more such agents.

The terms "therapeutic-effective" or "therapeutically-effective amount", as used herein, refer to the amount of the biologically active agent needed to stimulate or initiate the desired beneficial result. The amount of the biologically active agent employed in the coatings of the invention will be that amount necessary to deliver an amount of the biologically active agent needed to achieve the desired result. In practice, this will vary widely depending upon the particular biologically active agent being delivered, the site of delivery, and the dissolution and release kinetics for delivery of the biologically active agent into skin tissues.

The term "coating formulation", as used herein, means and includes a freely flowing composition or mixture, which is employed to coat a delivery surface, including one or more microprojections and/or arrays thereof.

The term "biocompatible coating", as used herein, means and includes a coating formed from a "coating formulation" that has sufficient adhesion characteristics and no (or minimal) adverse interactions with the biologically active agent.

The term "microprojections", as used herein, refers to piercing elements that are adapted to pierce or cut into and/or through the stratum corneum into the underlying epidermis layer, or epidermis and dermis layers, of the skin of a living animal, particularly a mammal and, more particularly, a human.

The term "microprojection member", as used herein, generally connotes a microprojection array comprising a plurality of microprojections arranged in an array for piercing the stratum corneum. The microprojection member can be formed by etching or punching a plurality of microprojections from a thin sheet and folding or bending the microprojections out of the plane of the sheet to form a configuration. The microprojection member can also be formed in other known manners, such as by forming one or more strips having microprojections along an edge of each of the strip(s), as disclosed in U.S. Pat. No. 6,050,988, which is hereby incorporated by reference in its entirety.

Microprojection members that can be employed with the present invention include, but are not limited to, the members disclosed in U.S. Pat. Nos. 6,083,196, 6,050,988 and 6,091,975, and U.S. Patent Application Pub. No. 2002/0016562, which are incorporated by reference herein in their entirety. As will be appreciated by one having ordinary skill in the art, where a microprojection array is employed, the dose of the therapeutic agent that is delivered can also be varied or manipulated by altering the microprojection array (or patch) size, density, etc.

As discussed above in the Background section, current manufacturing and packaging processes for delivery devices involving microprojections are problematic, especially where the microprojections are coated with a formulation by drying the formulation on the microprojections, as described in U.S. patent application Publication No. 2002/0128599. The formulation is usually an aqueous formulation. During the drying process, all volatiles, including water are mostly removed, however, the final solid coating still contains typically about 3% water. The presence of water can lead to deterioration of the biologically active agent in the formulation because of hydrolysis.

The current manufacturing and packaging processes are also problematic because oxygen is present during each phase. While the manufacturing phase is a relatively short period of time, the packaging and storage phase can be quite lengthy. Storage times of transdermal delivery systems are likely to be for lengthy periods of time before they are used (i.e., extended shelf life of several months is not uncommon). The biologically active agents in the coatings, therefore, are subject to oxidation and deterioration.

For purposes of this application, reference to the term "package" or "packaging" will be understood to also include reference to "storage" or "storing".

Accordingly, physical stabilization, especially minimizing the exposure of the biologically active agent formulations over time to oxidation and hydrolysis, is an important step in assuring efficacy of the therapeutic agents, particularly when the mode of delivery of the therapeutic agent is via a transdermal delivery device having a plurality of microprojections coated with an agent containing biocompatible coating.

The above noted publication, however, does not disclose a formulation of or technique for, physically stabilizing formulations of oxygen-sensitive biologically active agents, in particular, mitigating or eliminating the presence of oxygen during the packaging of transdermal delivery devices, and resultant unwanted oxidation of the biologically active agents. In particular, the noted publication does not disclose a formulation of, or technique for, physically stabilizing biologically active agents by manufacturing and/or packaging the biologically active agent-containing transdermal delivery devices in a dry inert atmosphere (essentially zero water content), which impart to the formulation stability against undesired changes over time due to oxidation.

Nor does the above noted publication disclose a formulation of or technique for, physically stabilizing formulations of water-sensitive biologically active agents, in particular, mitigating or eliminating the presence of water during the packaging of transdermal delivery devices, and resultant unwanted hydrolysis of the biologically active agents. In particular, the noted publication does not disclose a formulation of, or technique for, physically stabilizing biologically active agents by manufacturing and/or packaging the biologically active agent-containing transdermal delivery devices in a partial vacuum, which impart to the formulation stability against undesired changes over time due to hydrolysis.

Improved physical stability of such therapeutic formulations of biologically active agents provides not only the benefit of an increased storage or shelf life for the therapeutic agent itself, but enhances efficacy in that once stabilized in accordance with the compositions of and methods for formulating and delivering of the present invention, the therapeutic agents become useful in a greater range of possible formulations, and with a greater variety of therapeutic agent delivery means.

As indicated above, the present invention comprises compositions of and methods for formulating and delivering biologically active agents having enhanced physical stability, and wherein deterioration from the presence of oxygen and/or water is minimized and/or controlled. The compositions of and methods for formulating and delivering biologically active agent formulations further allow for the minimization and/or control of impurities and oxidative byproducts to yield a consistent and predictable composition. The compositions of and methods for formulating and delivering biologically active agent formulations of the present invention further facilitate their incorporation into a biocompatible coating which can be employed to coat a stratum-corneum piercing microprojection, or a plurality of stratum-corneum piercing microprojections of a delivery device, for delivery of the biocompatible coating through the skin of a subject, thus providing an effective means of delivering the biologically active agents.

The above noted publication, nor any other known reference, however, disclose a formulation of or technique for, physically stabilizing formulations of oxygen-sensitive biologically active agents, in particular, mitigating or eliminating the presence of oxygen during the packaging of transdermal delivery devices, and resultant unwanted oxidation of the biologically active agents. In particular, the noted publication, nor any other known reference disclose a formulation of or technique for, physically stabilizing biologically active agents by manufacturing and/or packaging the biologically active agent-containing transdermal delivery devices in a dry inert atmosphere (essentially zero water content), which impart to the formulation stability against undesired changes over time due to oxidation.

Nor does the above noted publication, nor any other known reference disclose a formulation of, or technique for, physically stabilizing formulations of water-sensitive biologically active agents, in particular, mitigating or eliminating the presence of water during the packaging of transdermal delivery devices, and resultant unwanted hydrolysis of the biologically active agents. In particular, the noted publication, nor any other known reference disclose a formulation of or technique for, physically stabilizing biologically active agents by manufacturing and/or packaging the biologically active agent-containing transdermal delivery devices in a partial vacuum, which impart to the formulation stability against undesired changes over time due to hydrolysis.

Improved physical stability of such therapeutic formulations of biologically active agents provides not only the benefit of an increased storage or shelf life for the therapeutic agent itself, but enhances efficacy in that once stabilized in accordance with the compositions of and methods for formulating and delivering of the present invention, the therapeutic agents become useful in a greater range of possible formulations, and with a greater variety of therapeutic agent delivery means.

According to one embodiment, the present invention comprises a biologically active agent formulation wherein the deterioration by oxygen and/or water is minimized and/or controlled by the manufacture and/or packaging of the biologically active agent formulation in a dry inert atmosphere. Preferably the biologically active agent is contained in a dry inert atmosphere in the presence of a desiccant. More preferably, the biologically active agent is contained in a dry inert atmosphere in the presence of a desiccant in a foil-lined chamber.

According to one embodiment, the present invention comprises a biologically active agent formulation wherein the deterioration by oxygen and/or water is minimized and/or controlled by the manufacture and/or packaging of the biologically active agent formulation in a partial vacuum. Preferably the biologically active agent is contained in a partial vacuum in the presence of a desiccant. More preferably, the biologically active agent is contained in a partial vacuum in the presence of a desiccant in a foil-lined chamber.

According to one embodiment, the present invention comprises a biologically active agent formulation wherein the deterioration by oxygen and/or water is minimized and/or controlled by the manufacture and/or packaging of the biologically active agent formulation in a dry inert atmosphere and a partial vacuum. Preferably the biologically active agent is contained in a dry inert atmosphere and a partial vacuum in the presence of a desiccant. More preferably, the biologically active agent is contained in a dry inert atmosphere and a partial vacuum in the presence of a desiccant in a foil-lined chamber.

Generally, in the noted embodiments of the present invention, the dry inert atmosphere is nitrogen, but can also be any other inert atmosphere known to those of skill in the art such as argon, helium, neon, krypton, carbon dioxide. For improved stability of the product, the inert atmosphere should be essentially zero water content. For example, nitrogen gas of essentially zero water content (dry nitrogen gas) can be prepared very simply by electrically controlled boiling of liquid nitrogen. Purge systems can be also used to reduce moisture or oxygen content.

Packaging under a partial vacuum is known to those skilled in the art. A preferred range for a partial vacuum is from about 0.01 to about 0.3 atmospheres.

As discussed above, the biologically active agent formulations are generally prepared as a solid coating by drying a formulation on the microprojection, as described in U.S. patent application Publication No. 2002/0128599. The formulation is usually an aqueous formulation. During a drying process, all volatiles, including water are mostly removed, however, the final solid coating still contains typically about 3% water.

The present invention reduces the oxygen and/or water content present in the formulations. Oxygen and/or water content are reduced by the use of a dry inert atmosphere and/or a partial vacuum. In a solid coating on a microprojection array, the drug is typically present in an amount of less than about 1 mg per unit dose. With the addition of excipients, the total mass of solid coating is less than 3 mg per unit dose. The array is usually present on an adhesive backing, which is attached to a disposable polymeric retainer ring. This assembly is packaged individually in a pouch or a polymeric housing. In addition to the assembly, this package contains a dead volume that represents a volume of at least 3 mL. This large volume (as compared to that of the coating) acts as a partial sink for water. For example, at 20 degree C., the amount of water present in a 3 mL atmosphere as a result of its vapor pressure would be about 0.05 mg at saturation, which is typically the amount of residual water that is present in the solid coating after drying. Therefore, storage in a dry inert atmosphere and/or a partial vacuum will further reduce the water content of the coating resulting in improved stability.

In addition, desiccants and oxygen absorbers can be incorporated in the packaging to further reduce oxygen and water content. The desiccant or oxygen absorber can be any known to those skilled in the art. Some common desiccants or oxygen absorbers include, but are not limited to calcium oxide, clay desiccant, calcium sulfate, and silica gel. The desiccant or oxygen absorber is preferably one that can be placed with the biologically active agent-containing formulation in the presence of an inert atmosphere in a foil-lined chamber.

Figure 6:
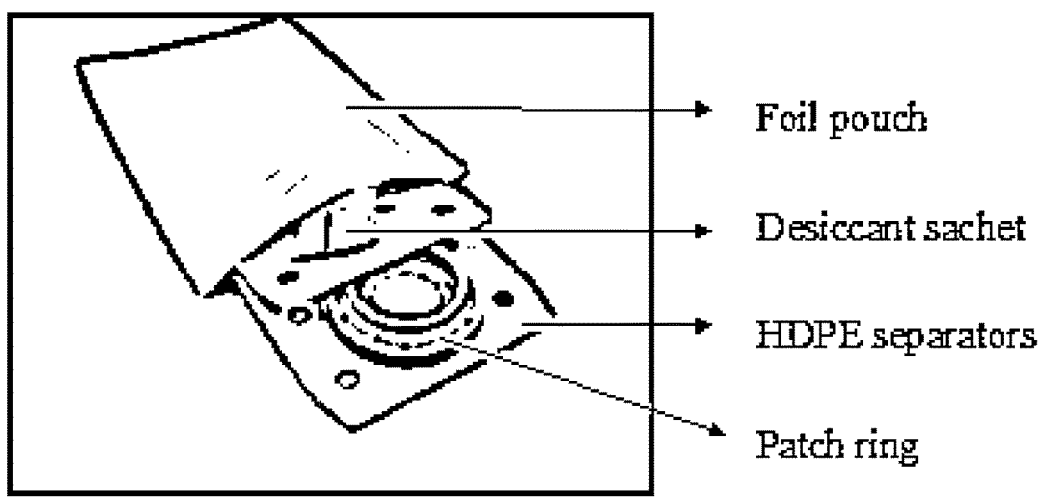
FIG. 6 is a perspective view of the microprojection array in foil packaging with a desiccant enclosed.

The biologically active agent formulation is preferably packaged in a foil-lined chamber after the biologically active agent formulation is prepared, and preferably after the biologically active agent formulation is coated onto the microprojection array delivery device. In one embodiment, the coated delivery device is placed in a foil-lined chamber as depicted in FIG. 6 and discussed below in the Example section in more detail. In this embodiment, a desiccant or oxygen absorber is attached to a foil lid and the chamber is purged with dry nitrogen prior to the foil delivery device-containing foil chamber being sealed by the foil lid.

Therapeutic Agents

A great number and variety of biologically active agents are known in the art to have therapeutic benefits when delivered appropriately to a patient having a condition upon which such therapeutic agents can exert a beneficial effect.

Suitable biologically active agents include therapeutic agents in all the major therapeutic areas including, but not limited to: anti-infectives, such as antibiotics and antiviral agents; analgesics, including fentanyl, sufentanil, remifentanil, buprenorphine and analgesic combinations; anesthetics; anorexics; antiarthritics; antiasthmatic agents, such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives, such as atenolol; ACE inhibitors, such as ranitidine; diuretics; vasodilators, including general, coronary, peripheral, and cerebral; central nervous system stimulants; cough and cold preparations; decongestants; diagnostics; hormones, such as parathyroid hormone; hypnotics; itnmunosuppressants; muscle relaxants; parasympatholytics; parasympathomimetrics; prostaglandins; proteins; peptides; psychostimulants; sedatives; and tranquilizers. Other suitable agents include vasoconstrictors, anti-healing agents and pathway patency modulators.

Further specific examples of agents include, without limitation, growth hormone release hormone (GHRH), growth hormone release factor (GHRF), insulin, insultropin, calcitonin, octreotide, endorphin, TRN, NT-36 (chemical name: N-[[(s)-4-oxo-2-azetidinyl]carbonyl]-L-histidyl-L-prolinamide), liprecin, pituitary hormones (e.g., HGH, HMG, desmopressin acetate, etc), follicle luteoids, aANF, growth factors such as growth factor releasing factor (GFRF), bMSH, GH, somatostatin, bradykinin, somatotropin, platelet-derived growth factor releasing factor, asparaginase, bleomycin sulfate, chymopapain, cholecystolcinin, chorionic gonadotropin, erythropoietin, epoprostenol (platelet aggregation inhibitor), glucagon, HCG, hirulog, hyaluronidase, interferon alpha, interferon beta, interferon gamma, interleukins, interleukin-10 (IL-10), erythropoietin (EPO), granulocyte macrophage colony stimulating factor (GM-CSF), granulocyte colony stimulating factor (G-CSF), glucagon, leutinizing hormone releasing hormone (LHRH), LHRH analogs (such as goserelin, leuprolide, buserelin, triptorelin, gonadorelin, and napfarelin, menotropins (urofollitropin (FSH) and LH)), oxytocin, streptokinase, tissue plasminogen activator, urokinase, vasopressin, deamino [Val4, D-Arg8] arginine vasopressin, desmopressin, corticotropin (ACTH), ACTH analogs such as ACTH (1-24), ANP, ANP clearance inhibitors, angiotensin II antagonists, antidiuretic hormone agonists, bradykinn antagonists, ceredase, CSI's, calcitonin gene related peptide (CGRP), enkephalins, FAB fragments, IgE peptide suppressors, IGF-1, neurotrophic factors, colony stimulating factors, parathyroid hormone and agonists, parathyroid hormone antagonists, parathyroid hormone (PTH), PTH analogs such as PTH (1-34), prostaglandin antagonists, pentigetide, protein C, protein S, renin inhibitors, thymosin alpha-1, thrombolytics, TNF, vasopressin antagonists analogs, alpha-1 antitrypsin (recombinant), and TGF-beta.

The biologically active agent can also comprise a vaccine, including viruses and bacteria, protein-based vaccines, polysaccharide-based vaccine, nucleic acid-based vaccines, and other antigenic agents. Suitable antigenic agents include, without limitation, antigens in the form of proteins, polysaccharide conjugates, oligosaccharides, and lipoproteins. These subunit vaccines in include *Bordetella pertussis* (recombinant PT accince—acellular), *Clostridium tetani* (purified, recombinant), *Corynebacterium diptheriae* (purified, recombinant), *Cytomegalovirus* (glycoprotein subunit), Group A *streptococcus* (glycoprotein subunit, glycoconjugate Group A polysaccharide with tetanus toxoid, M protein/peptides linke to toxing subunit carriers, M protein, multivalent type-specific epitopes, cysteine protease, C5a peptidase), Hepatitis B virus (recombinant Pre Si, Pre-S2, S, recombinant core protein), Hepatitis C virus (recombinant—expressed surface proteins and epitopes), Human papillomavirus (Capsid protein, TA-GN recombinant protein L2 and E7 [from HPV-6], MEDI-501 recombinant VLP Li from HPV-11, Quadrivalent recombinant BLP Li [from HPV-6], HPV-11, HPV-16, and HPV-18, LAMP-E7 [from HPV-16]), *Legionella pneumophila* (purified bacterial survace protein), *Neisseria meningitides* (glycoconjugate with tetanus toxoid), *Pseudomonas aeruginosa* (synthetic peptides), Rubella virus (synthetic peptide), *Streptococcus pneumoniae* (glyconconjugate [1, 4, 5, 6B, 9N, 14, 18C, 19V, 23F] conjugated to meningococcal B OMP, glycoconjugate [4, 6B, 9V, 14, 18C, 19F, 23F] conjugated to CRM197, glycoconjugate [1, 4, 5, 6B, 9V, 14, 18C, 19F, 23F] conjugated to CRM1970, *Treponema pallidum* (surface lipoproteins), Varicella zoster virus (subunit, glycoproteins), and *Vibrio cholerae* (conjugate lipopolysaccharide).

Whole virus or bacteria include, without limitation, weakened or killed viruses, such as cytomegalo virus, hepatitis B virus, hepatitis C virus, human papillomavirus, rubella virus, and varicella zoster, weakened or killed bacteria, such as *bordetella pertussis, clostridium tetani, corynebacterium*

*diptheriae*, group A *streptococcus, legionella pneumophila, neisseria meningitdis, pseudomonas aeruginosa, streptococcus pneumoniae, treponema pallidum*, and *vibrio cholerae*, and mixtures thereof.

Additional commercially available vaccines, which contain antigenic agents, include, without limitation, flu vaccines, lyme disease vaccine, rabies vaccine, measles vaccine, mumps vaccine, chicken pox vaccine, small pox vaccine, hepatitus vaccine, pertussis vaccine, and diptheria vaccine.

Vaccines comprising nucleic acids include, without limitation, single-stranded and double-stranded nucleic acids, such as, for example, supercoiled plasmid DNA; linear plasmid DNA; cosmids; bacterial artificial chromosomes (BACs); yeast artificial chromosomes (YACs); mammalian artificial chromosomes; and RNA molecules, such as, for example, mRNA. The size of the nucleic acid can be up to thousands of kilobases. In addition, in certain embodiments of the invention, the nucleic acid can be coupled with a proteinaceous agent or can include one or more chemical modifications, such as, for example, phosphorothioate moieties. The encoding sequence of the nucleic acid comprises the sequence of the antigen against which the immune response is desired. In addition, in the case of DNA, promoter and polyadenylation sequences are also incorporated in the vaccine construct. The antigen that can be encoded include all antigenic components of infectious diseases, pathogens, as well as cancer antigens. The nucleic acids thus find application, for example, in the fields of infectious diseases, cancers, allergies, autoimmune, and inflammatory diseases.

Suitable immune response augmenting adjuvants which, together with the vaccine antigen, can comprise the vaccine include aluminum phosphate gel; aluminum hydroxide; algal glucan: b-glucan; cholera toxin B subunit; CRL1005: ABA block polymer with mean values of x=8 and y=205; gamma inulin: linear (uribranched) B-D(2->1) polyfructofuranoxyl-a-D-glucose; Gerbu adjuvant: N-acetylglucosamine-(1-4)-N-acetylmuramyl-L-alanyl-Dglutamine (GMDP), dimethyl dioctadecylammonium chloride (DDA), zinc L-proline salt complex (Zn-Pro-8); Imiquimod (1-(2-methypropyl)-1H-imidazo[4,5-c]quinolin-4-amine; ImmThero: N-acetylglucoaminyl-Nacetylmuramyl-L-Ala-D-isoGlu-L-Ala-glycerol dipalmitate; MTP-PE liposomes: C59H108N6O19PNa-3H2O (MTP); Murametide: Nac-Mur-L-Ala-D-Gln-OCH3; Pleuran: b-glucan; QS-21; S-28463: 4-amino-a, a-dimethyl-1H-imidazo[4,5-c]quinoline-1-ethanol; sclavo peptide: VQGEESNDK-HC1 (IL-lb 163-171 peptide); and threonyl-MDP (Tennurtide0): N-acetyl muramyl-L-threonyl-D-isoglutamine, and interleukine 18, IL-2 IL-12, IL-15, Adjuvants also include DNA oligonucleotides, such as, for example, CpG containing oligonucleotides. In addition, nucleic acid sequences encoding for immuno-regulatory lymphokines such as IL-18, IL-2 IL-12, IL-15, IL-4, IL10, gamma interferon, and NF kappa B regulatory signaling proteins can be used.

In another embodiment, suitable counterions are added to the formulation to further improve the stability of the formulation. Examples of counterions suitable for formulation with net positively charged biologically active agent include, but are not limited to, acetate, propionate, butyrate, pentanoate, hexanoate, heptanoate, levulinate, chloride, bromide, citrate, succinate, maleate, glycolate, gluconate, glucuronate, 3-hydroxyisobutyrate, 2-hydroxyisobutyrate, lactate, malate, pyruvate, fumarate, tartarate, tartronate, nitrate, phosphate, benzene sulfonate, methane sulfonate, sulfate, and sulfonate. Preferably, the counterion mixture is added to the biologically active agent formulation in an amount sufficient to neutralize the net charge of the biologically active agent. However, an excess of counterion mixture (either as the acid or the conjugate acid-base) can be added to the biologically active agent.

In another embodiment of the present invention, the biologically active agent possesses a net negative charge, and counterion mixture preferably possesses a net positive charge at the solution pH. Examples of negatively-charged biologically active agents include insulin in the pH range 6-14, VEGF in the pH range 6-14, and insulinotropin in the pH range 6-14.

In the above embodiment, examples of counterions suitable for formulation with net negatively charged biologically active agents include, but are not limited to, sodium, potassium, calcium, magnesium, ammonium, monoethanolamine, diethanolamine, triethanolamine, tromethamine, lysine, histidine, arginine, morpholine, methylglucamine, and glucosamine. The counterion or counterion mixture is preferably added to the biologically active agent formulation in an amount sufficient to neutralize the net charge of the biologically active agent. However, an excess of counterion or counterion mixture (either as the base or the conjugate acid-base) can be added to the biologically active agent.

In a particularly preferred embodiment of the present invention, the biologically active agent comprises hPTH. It is particularly preferred to stabilize the hPTH formulation in an inert atmosphere, preferably nitrogen.

In a preferred embodiment, the biologically active agent and counterion (or counterion mixture) is formulated as a solution or suspension in an appropriate solvent. Suitable solvents include water, DMSO, ethanol, isopropanol, DMF, acetonitrile, N-methyl-2-pyrollidone, and mixtures thereof. In addition, the biologically active agent can be in solution or suspension in a polymeric vehicle, such as EVA or PLGA. As is known in the art, additional stabilizing additives, such as sucrose and trehalose, may be present in the formulation.

Various other additives that aid in the delivery, stability or efficacy of the biologically active agents of the present invention can also be added to the formulations of the invention. Thus, the compositions and formulations of the present invention can contain suitable adjuvants, excipients, solvents, salts, surfactants, buffering agents and other components. Examples of such additives can be found in U.S. patent application Ser. Nos. 10/880,702 and 10/970,890, the disclosures of which are incorporated by reference herein.

In additional embodiments of the present invention, the biologically active agents, which have been stabilized by minimizing or eliminating exposure to oxygen after the agents are formulated as a solution or suspension, and then can be dried, freeze-dried (or lyophilized), spray dried or spray-freeze dried to stabilize for storage.

In another preferred embodiment of the present invention, the biologically active agent formulations, which have been stabilized by minimizing or eliminating exposure to oxygen and water, are included in biocompatible coating formulations used to coat a stratum-corneum piercing microprojection, or plurality of a stratum-corneum piercing microprojections, or an array thereof, or delivery device, for delivery of the biologically active agent through the skin of a patient. Compositions of and methods for formulating biocompatible coatings are described in U.S. Patent Application Pub. No. 2002/0177839 to Cormier et al; U.S. Patent Application Pub. No. 2004/0062813 to Cormier et al and U.S. Patent Application Pub. No. 2002/0132054 to Trautman et al, the disclosures of which are incorporated herein by reference.

For biologically active agent formulations, particularly those therapeutic agents which comprise or include relatively high molecular weight polypeptides or proteins, it is preferred to formulate the biocompatible coating containing the therapeutic agent, such that a water-soluble, biocompatible polymer, is attached to, or associated with, the polypeptide or protein. A particularly preferred method is to form a conjugate of the polymer with the polypeptide or protein. The attachment of a polymer, such as PEG, to proteins and polypeptides typically results in improved solubility, improved physical and chemical stability, lower aggregation tendency and enhanced flow characteristics. Compositions of and methods for formulating biocompatible coatings having polymer conjugates of protein and polybiologically active agents are disclosed in U.S. patent application Ser. No. 10/972,231, the disclosures of which is incorporated herein by reference.

Other compositions of and methods for formulating and delivering protein-based therapeutic agent formulations are disclosed in U.S. Patent Application No. 60/585,276, filed Jul. 1, 2004, the disclosure of which is incorporated by reference herein. The noted application discloses compositions of and methods for formulating hormone therapeutic agents having a desired pharmacokinetic delivery profile, as well as the formulation of biocompatible coatings therewith.

in accordance with one embodiment of the invention, a method for delivering stable biologically active agent formulations comprises the following steps: (i) providing a microprojection member having a plurality of microprojections, (ii) providing a stabilized formulation of biologically active agent; (iii) forming a biocompatible coating formulation that includes the formulation of stabilized biologically active agent, (iv) coating the microprojection member with the biocompatible coating formulation to form a biocompatible coating; (v) stabilizing the biocompatible coating by drying; and (vi) applying the coated microprojection member to the skin of a subject.

Figure 5:
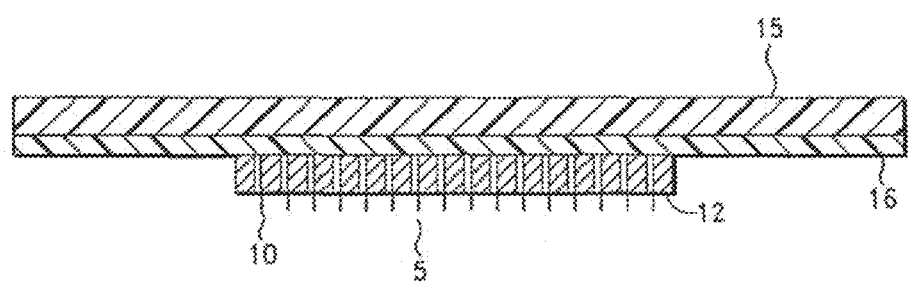
FIG. 5 is a side sectional view of a microprojection array illustrating an alternative embodiment of the invention, wherein different biocompatible coatings may be applied to different microprojections.

FIG. 1 illustrates one embodiment of a stratum corneum-piercing microprojection array for use with the compositions and methods for formulating and delivering of the present invention. As shown in FIG. 1, the microprojection array 5 includes a plurality of microprojections 10. The microprojections 10 extend at substantially a 90 degree angle from a sheet 12 having openings 14. As shown in FIG. 5, the sheet 12 can be incorporated in a delivery patch including a backing 15 for the sheet 12. The backing 15 can further include an adhesive 16 for adhering the backing 15 and microprojection array 5 to a patient's skin. In this embodiment, the microprojections 10 are formed by either etching or punching a plurality of microprojections 10 out of a plane of the sheet 12.

The microprojection array 5 can be manufactured of metals, such as stainless steel, titanium, nickel titanium alloys, or similar biocompatible materials, such as plastics. In a preferred embodiment, the microprojection array is constructed of titanium. Metal microprojection members are disclosed in Trautman et al., U.S. Pat. No. 6,038,196; Zuck U.S. Pat. No. 6,050,988; and Daddona et al., U.S. Pat. No. 6,091,975, the disclosures of which are herein incorporated by reference.

Other microprojection members that can be used with the present invention are formed by etching silicon, by utilizing chip etching techniques or by molding plastic using etched micro-molds. Silicon and plastic microprojection members are disclosed in Godshall et al., U.S. Pat. No. 5,879,326, the disclosure of which is incorporated herein by reference.

With such microprojection devices, it is important that the biocompatible coating having the biologically active agent is applied to the microprojections homogeneously and evenly, preferably limited to the microprojections themselves. This enables dissolution of the biologically active agent in the interstitial fluid once the device has been applied to the skin and the stratum corneum pierced. Additionally, a homogeneous coating provides for greater mechanical stability both during storage and during insertion into the skin. Weak and/or discontinuous coatings are more likely to flake off during manufacture and storage, and to be wiped of the skin during application.

Additionally, optimal stability and shelf life of the agent is attained by a biocompatible coating that is solid and substantially dry. However, the kinetics of the coating dissolution and agent release can vary appreciably depending upon a number of factors. It will be readily appreciated that in addition to being storage stable, the biocompatible coating should permit desired release of the therapeutic agent.

Depending on the release kinetics profile, it may be necessary to maintain the coated microprojections in piercing relation with the skin for extended periods of time (e.g., up to about 8 hours). This can be accomplished by anchoring the microprojection member to the skin using adhesives or by using anchored microprojections, such as described in U.S. Pat. No. 6,230,051, to Cormier et al, the disclosure of which is incorporated by reference herein in its entirety.

Compositions of and methods for formulating biocompatible coatings are described, for example, in U.S. Patent Application Pub. Nos. 2002/0128599, 2002/0177839 and 2004/0115167, the disclosures of which are incorporated herein by reference.

In one embodiment of the present invention, a dip-coating process is employed to coat the microprojections by partially or totally immersing the microprojections into the biocorrpatible coating solution containing the stable biologically active agent formulation. Alternatively, the entire device can be immersed into the biocompatible coating solution.

In many instances, the stable therapeutic agent within the coating can be very expensive. Therefore, it may be preferable to only coat the tips of the microprojections. Microprojection tip coating apparatus and methods are disclosed in Trautman et al., US Patent Application Pub. No. 2002/0132054. The noted publication discloses a roller coating mechanism that limits the coating to the tips of the microprojection.

As described in the Trautman et al publication, the coating device only applies the coating to the microprojections and not upon the substrate/sheet that the microprojections extend from. This may be desirable in the case where the cost of the active (or beneficial) agent is relatively high and therefore the coating containing the beneficial agent should only be disposed onto parts of the microprojection array that will pierce beneath the patient's stratum comeum layer.

The noted coating technique has the added advantage of naturally forming a smooth coating that is not easily dislodged from the microprojections during skin piercing. The smooth cross section of the microprojection tip coating is more clearly shown in FIG. 2A.

Figure 2:
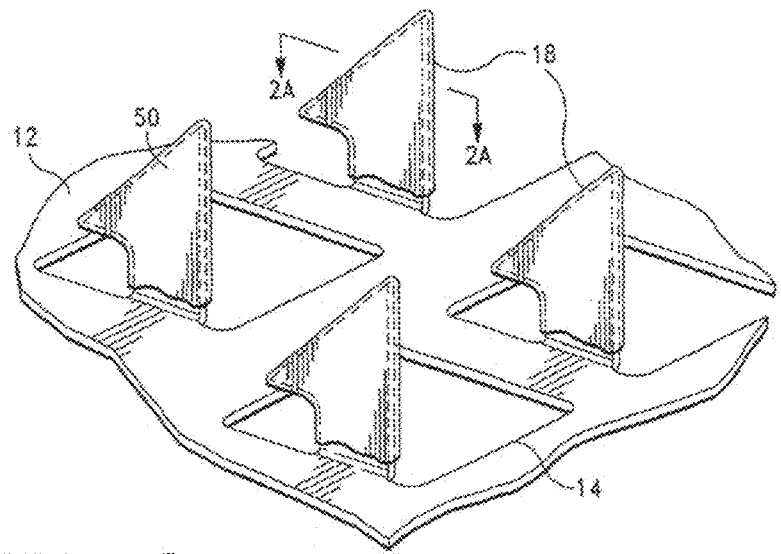
FIG. 2 is a perspective view of the microprojection array shown in FIG. 1 with a biocompatible coating deposited onto the microprojections.
Figure 2A:
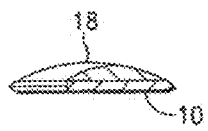
FIG. 2A is a cross-sectional view of a single microprojection taken along line 2A-2A in FIG. 1.

Other coating techniques, such as microfluidic spray or printing techniques, can also be used to precisely deposit a coating 18 on the tips of the microprojections 10, as shown in FIG. 2.

Other coating methods that can be employed in the practice of the present invention include spraying the coating solution onto the microprojections. Spraying can encompass formation of an aerosol suspension of the coating composition. In one embodiment, an aerosol suspension forming a droplet size of about 10 to about 200 picoliters is sprayed onto the microprojections and then dried.

The microprojections 10 can further include means adapted to receive and/or increase the volume of the coating 18 such as apertures (not shown), grooves (not shown), surface irregularities (not shown), or similar modifications, wherein the means provides increased surface area upon which a greater amount of coating may be deposited.

Figure 3:
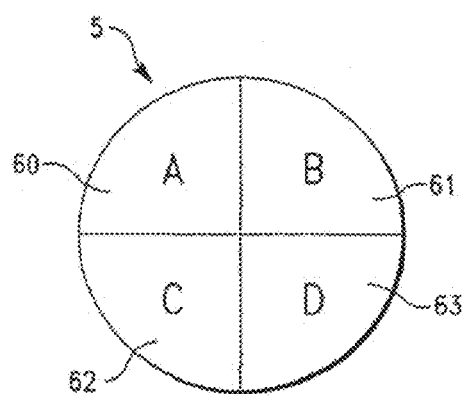
FIG. 3 is a schematic illustration of a skin proximal side of a microprojection array, illustrating the division of the microprojection array into various portions, according to the invention.
Figure 4:
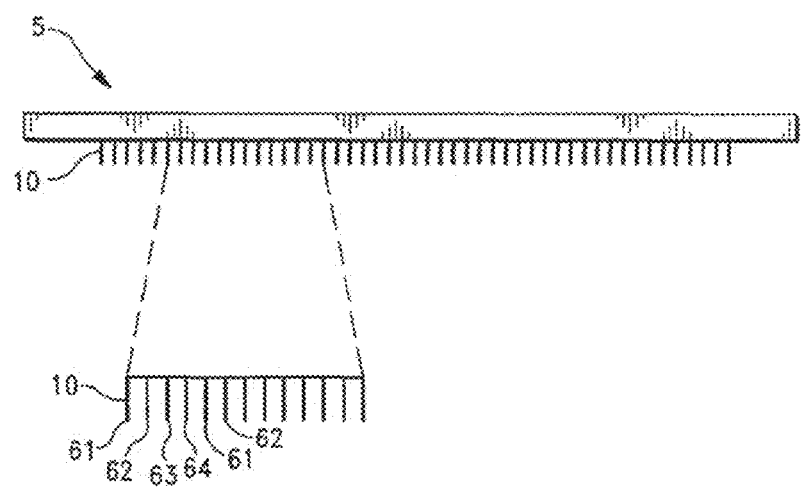
FIG. 4 is a side plane view of a skin proximal side of a microprojection array, illustrating the division of the microprojection array into various portions, according to the invention.

Referring now to FIGS. 3 and 4, there is shown an alternative embodiment of a microprojection array 5. As shown in FIG. 3, the microprojection array 5 may be divided into portions illustrated at 60-63, wherein a different coating is applied to each portion, thereby allowing a single microprojection array to be utilized to deliver more than one beneficial agent during use.

Referring now to FIG. 4, there is shown a cross-sectional view of the microprojection array 5, wherein a "pattern coating" has been applied to the microprojection array 5. As shown, each of the microprojections 10 can be coated with a different bio compatible coating and/or a different therapeutic agent, as indicated by reference numerals 61-64. That is, separate coatings are applied to the individual microprojections 10. The pattern coating can be applied using a dispensing system for positioning the deposited liquid onto the surface of the microprojection array.

The quantity of the deposited liquid is preferably in the range of 0.1 to 20 nanoliters/microprojection. Examples of suitable precision-metered liquid dispensers are disclosed in U.S. Pat. Nos. 5,916,524, 5,743,960, 5,741,554 and 5,738,728, the disclosures of which are incorporated herein by reference.

Microprojection coating solutions can also be applied using ink jet technology using known solenoid valve dispensers, optional fluid motive means and positioning means which are generally controlled by use of an electric field. Other liquid dispensing technology from the printing industry or similar liquid dispensing technology known in the art can be used for applying the pattern coating of this invention.

In yet another preferred embodiment, the process of applying a biocompatible coating containing a biologically active agent of the invention to at least one stratum-corneum piercing microprojection of a microprojection member, more preferably, to a plurality of such stratum-corneum piercing microprojections, includes the step of further stabilizing the biocompatible coating by drying. The drying step can occur at ambient (room) temperatures and conditions, or can employ temperatures in the range of 4 to 50° C.

Suitable drying methods and apparatus are disclosed in U.S. Patent Application No. 60/572,861, filed May 19, 2004, the disclosure of which is incorporated herein by reference.

According to the invention, a multitude of biologically active active agents can be subjected to the formulation process and methods of the invention to provide highly stable biologically active formulations. In a preferred embodiment of the invention, the therapeutic agent comprises hPTH or an analog thereof.

EXAMPLES

The following studies and examples illustrate the formulations, methods and processes of the invention. The examples are for illustrative purposes only and are not meant to limit the scope of the invention in any way.

Example 1

This study demonstrates how a dry inert environment allows for maintaining stability of hPTH(1-34). A delivery device having stratum corneum piercing microprojections coated with a formulation of hPTH(1-34) was prepared. The primary packaging for all dosages of the systems was a heat sealed foil pouch purged with nitrogen gas.

The storage environment within the sealed foil pouches, was assessed by performing head-space gas analysis, whereby a head-space gas sample is obtained and subjected to quadruple mass spectroscopy analysis for the identification and quantitation of low molecular weight volatile compounds, including moisture, oxygen, nitrogen, and argon.

In addition, three foil pouches packaged with fully assembled systems (without desiccant) were assessed in the same manner. Results indicate that the level of moisture inside the pouch is quite variable from pouch to pouch, 26% to 45% RH (at 22° C. in Table 1), which corresponds to the water content of 3.5% and 7%, respectively. Notably, all samples reached 100% RH if stored at 5° C. Such humidity is considered high and may be detrimental to hPTH stability. Therefore, reducing head-space humidity is necessary.

In one process, the retainer rings were pre-dried (rings dried in vacuo at 60° C. for at least 48 h prior to assembly) or packaged without a retainer ring or adhesive (Table 2). The moisture and oxygen levels were substantially reduced –2.2% RH in the sample packaged with a pre-dried retainer ring. In the system without the adhesive or ring, the moisture level was also reduced to 9% RH. Therefore, the results indicate that the retainer ring is a source of moisture and oxygen; the ring contains a substantial amount of adsorbed water and oxygen that desorbs into the head-space gas once the pouch has been purged and sealed. This illustrates that pre-drying the ring effectively removes the desorbed oxygen and moisture from the ring prior to pouching.

In a different process, desiccant was added directly to the pouch, using the 4 A molecular sieve desiccant of two different sizes and configurations: 1) 3.5 g Minipax molecular sieves packaged in Tyvek sachets, and 2) 125 mg Desimax adhesive labels affixed to the inside walls of the foil pouch. The head-space results (Table 3) indicate that the 3.5 g 4 A molecular sieves are effective in reducing pouch humidity while the smaller desiccant labels (0.25 g) perform poorly. Desiccants were manually inserted and handled in ambient air prior to pouching and the smaller desiccant labels may have reached near moisture saturation even before packaging.

Since the retainer ring is a source of moisture and a sufficient amount of desiccant is needed, the internal vapor level was assessed of 12 Macroflux® systems in the current packaging condition, i.e., coated array, Tyvek pouch, 3 A, 3.5 g desiccant sachet, foil pouch and N2 purge. As summarized in Table 4, % RH is extremely low, <1%, in all 12 samples, indicating the desiccant is functioning consistently to maintain the internal head space very dry although the retainer ring can release variable amounts of moisture during storage.

Macroflux® PTH systems were sealed in foil pouches in one of the three packaging configurations: 1) the coated array only with N2 purge; 2) the fully assembled system (coated array+adhesive+retainer ring) with N2 purge; 3) the fully assembled system+a 3.5 g desiccant sachet with N2 purge. All systems were stored at 25° C. for 12 months. Samples were removed at 3, 6, 9, and 12 months for reverse RHPLC analysis.

FIG. 7 summarizes % PTH purity change with time. The fully packaged systems containing desiccant performed the best. Systems containing only the coated array performed well and quite comparable to the fully packaged systems containing desiccant. According to the head-space analysis mentioned above, the environmental % RH in the system with desiccant is <1% while that in the system without desiccant can be as high as 50%. The coated-array-only system also offers a dry environment, <10% RH (Table 2), as it lacks the retainer ring which is the main source of moisture.

Water (or moisture) is known to be able to adversely affect peptide/protein stability in the solid-state formulation. The humid environment enhances moisture adsorption by the hygroscopic amorphous coating and may increase the amount of residual water vapor available to hydrolyze and/or plasticize the amorphous matrix, thereby reducing the glass transition temperature and increasing molecular mobility as well as the rate of all chemical reactions in the solid. As the foregoing example illustrates, various embodiments of the present invention provide an effective means for providing a dry environment.

TABLE 1

Space Analysis for Standard Packaging Conditions (without Desiccant)

| RESIDUAL GAS ANALYSIS | | STANDARD PACKAGING CONDITIONS | | | Mean | s.. | CV |
|---|---|---|---|---|---|---|---|
| POUCH PRESSURE | ton | 684 | 586 | 749 | 673 | 82 | 12.2% |
| NITROGEN | ppm | 987,275 | 987,352 | 984,972 | 986,533 | 1,352 | 0.1% |
| OXYGEN | ppm | 3,259 | 3,289 | 2,434 | 2,994 | 485 | 16.2% |
| ARGON | ppm | 169 | 158 | 133 | 153 | 18 | 12.0% |
| CO2 | ppm | 119 | 124 | 134 | 126 | 8 | 6.1% |
| MOISTURE | PPm | 9,052 | 8,960 | 12,223 | 10,078 | 1,858 | 18.4% |
| HYDROGEN | ppm | 126 | 116 | 104 | 115 | 11 | 9.6% |
| HELIUM | ppm | ND | ND | ND | ND | ND | ND |
| FLUOROCARBONS | ppm | ND | ND | ND | ND | ND | ND |
| CALCULATED RH at 22° C. | | 31% | 26% | 45% | 34% | 10% | 29% |
| CALCULATED RH at 5° C. | | 100% | 98% | 100% | 100% | | |

*RH calculated at a temperature of 22° C., samples analyzed at ambient temperature.

TABLE 2

Effect of Assembly Components on Pouch Head Space

| RESIDUAL GAS ANALYSIS | | +pre dried ring | Array Only |
|---|---|---|---|
| POUCH PRESSURE | torr | 651 | 730 |
| NITROGEN | ppm | 998,805 | 997,396 |
| OXYGEN | PPm | 514 | 246 |
| ARGON | PPm | 53 | 44 |
| CO2 | PPm | 60 | 37 |
| MOISTURE* | PPm | 514 | 2,212 |
| HYDROGEN | PPm | 54 | 65 |
| HELIUM | PPm | ND | ND |
| FLUOROCARBONS | PPm | ND | ND |
| *CALCULATED RH | 22° C. | 2.2% | 9.0% |

TABLE 3

Effect of Added Desiccant on Pouch Head Space

| RESIDUAL GAS ANALYSIS | | +Desiccant (2 × 125 mg labels) | +Desiccant (3.5 g sachet) |
|---|---|---|---|
| POUCH PRESSURE | ton | 736 | 624 |
| NITROGEN | ppm | 977,856 | 982,666 |
| OXYGEN | ppm | 7,463 | 15,335 |
| ARGON | ppm | 367 | 617 |
| CO2 | ppm | 207 | 1,237 |
| MOISTURE* | ppm | 14,012 | 41 |
| HYDROGEN | ppm | 95 | 47 |
| HELIUM | PPm | ND | ND |
| FLUOROCARBONS | PPm | ND | ND |
| *CALCULATED RH | 22° C. | 51% | 0.12% |

Example 2

This example applies a delivery device having stratum corneum-piercing microprojections coated with a formulation of hBNP(1-32) (human b-type natriuretic peptide). Table 5 outlines the experimental stability study design for this example. The effect of reducing moisture and oxygen was assessed within the sealed pouch by addition of desiccant, oxygen absorbers or pre-drying the system components prior to final packaging. An additional forced degradation parameter is terminal sterilization which was assessed to generate accelerated stability data. Systems were packaged into each of the five packaging configurations outlined in Table 6 and subjected to e-beam treatment at a dose of 15 or 21 kGy and ambient temperature. Long-term stability samples for Groups A and B were stored at 2-8° C. or 25° C. and ambient humidity for up to 12 months with 5 time points. All other groups were stored at 25° C. and ambient humidity for one month. One sample from each group was submitted for head space analysis. All other samples were analyze by RP-HPLC for chemical stability by RPHPLC and were compared to similarly packaged non-irradiated shipping controls.

The head space data is summarized in Table 7 along with the details of the packaging and treatment conditions. The moisture vapor concentrations were converted to % RH assuming 760 ton total pouch pressure and 5 or 25° C. The non-irradiated shipping control (sample #1) was measured in triplicate to determine an estimation of the repeatability of the measurement system_For all gases detected at >500 ppm

TABLE 4

Internal Head Space Analysis on Macroflue PTH Systems in Current Packaging Configuration
(Coated array, Tyvek pouch, 3A, 3.5 g Desiccant Sachet, Foil Pouch, N2 Purge)

| RESIDUAL GAS ANALYSIS | | 1 | 2 | 3 | 4 | 5 | 6 | 7 | 8 | 9 | 10 | 11 | 12 |
|---|---|---|---|---|---|---|---|---|---|---|---|---|---|
| POUCH PRESSURE | ton | 190 | 180 | 190 | 187 | 190 | 190 | 191 | 191 | 191 | 187 | 187 | 191 |
| NITROGEN | % | 98.1 | 98.1 | 98.9 | 98.9 | 98.4 | 98.4 | 97.3 | 97.3 | 97.9 | 97.9 | 98.2 | 98.2 |
| OXYGEN | % | 1.79 | 1.77 | 1.00 | 1.00 | 1.54 | 1.54 | 2.52 | 2.52 | 2.04 | 2.02 | 1.67 | L68 |
| ARGON | ppm | 784 | 785 | 431 | 435 | 688 | 666 | 1,112 | 1,102 | 888 | 899 | 739 | 741 |
| CO2 | ppm | <100 | <100 | <100 | <100 | <100 | <100 | | <100 | <100 | <100 | <100 | <100 |
| MOISTURE* | ppm | <100 | <100 | <100 | <100 | 162 | 258 | <100 | <100 | <100 | <100 | 352 | 275 |
| HYDROGEN | ppm | <100 | <100 | <100 | <100 | <100 | <100 | <100 | <100 | <100 | <100 | <100 | <100 |
| *CALCULATED RH 22° C. | | <1% | <1% | <1% | <1% | <1% | <1% | <1% | <1% | <1% | <1% | <2% | <1% | the repeatability was ~1% and for gases detected at levels <500 ppm the repeatability was ~10%.

The level of moisture for all samples containing desiccant are in-line with prior head space analysis from similarly packaged systems without Tyvek (~100 ppm) indicating that the addition of theTyvek pouch does not introduce a significant amount of moisture into the pouch head space. The level of oxygen, however is slightly higher than previously observed for a comparable system 0.2-0.3% vs 0.5% for this study prior to irradiation treatment. Following irradiation of the control system (packaging configuration A), the level of moisture appears unchanged, while the oxygen drops by a factor of ten and the hydrogen increases by a factor of 25. Interaction of the e-beam radiation with the polymeric species in the pouch (Tyvek and/or polycarbonate ring) to generate free-radicals and hydrogen as a by-product can reduce oxygen levels. The free-radicals that are generated can then react with oxygen in the head space to form reactive peroxy radicals resulting in oxidative degradation of the peptide The two samples packaged under vacuum (sample #2 and #3) were less effective in purging the pouch of oxygen or, to a lesser extent, moisture. These samples had roughly 30 fold more oxygen in the head space following irradiation, which may have been even higher prior to irradiation. Samples 5, 6 and 7 had no detectable levels of oxygen most likely due to the vacuum pre-treatment of the desiccant followed by nitrogen backfill for Sample 5, the and the lack of retainer rings for Samples 6 and 7, which are known to be a large source of oxygen. The somewhat higher moisture level (11% RH is still considered very dry) detected in Sample 6 is due to the absence of desiccant. Sample #7 (untreated desiccant and no retainer ring) had no detectable level of oxygen. In sample 7, oxygen released by the desiccant can be, consumed by free-radicals following e-beam treatment, notwithstanding the absence of a retainer ring.

Three samples from each packaging condition were submitted for RP-HPLC purity analysis immediately following e-beam treatment at T=0. The samples were averaged together and are summarized in FIG. 8 below and the results are compared to the head space moisture and oxygen in Table 8. The degradation profile for each condition is summarized in FIG. 9.

Purity decreases 2-3% following e-beam treatment at 15 or 21 kGy, this decrease is further exacerbated by increased levels of moisture in the pouch and to a lesser extent, high levels of oxygen. In addition to oxidation as the major degradation species, the acetate/citrate modifications observed at high retention times on the HPLC were also equally prevalent for this study. The modifications are a collection of several smaller peaks that are combined to give the reported value. These levels of acetate modifications have not been observed previously under similar e-beam treatment conditions (FIG. 10). One difference between the samples in present study is the Tyvek inner pouches (except sample #7) while samples in previous studies were packaged without Tyvek. However, it is unlikely that Tyvek itself causes any additional acetate/citrate modifications as sample #7, packaged without Tyvek contains approximately the same level of degradation in this region (2.0%) as other samples packaged with Tyvek (average=2.2%).

Samples from each pouching/irradiation condition were stored for 4 weeks at 2-8 or 25° C. n=3 samples for each condition were analyzed by RP-HPLC and an average peak area percentage is presented in the figures below. FIG. 11 compares the T=0 total peak area hBNP purity values with the 1M stability data packaged under nitrogen purge or vacuum.

The non-irradiated controls were also stored under accelerated temperature conditions of 40° C. for comparison. The data indicate that in addition to damaging the peptide at T4) during the irradiation process, e-beam treatment also increase the rate of degradation to well above the accelerated storage temperature of 40° C. for the non-irradiated controls (light blue bar in FIG. 11). The degradation profiles for the one month samples is presented in FIG. 12 and is compared to the T=0 data for each condition.

The major degradation species for each condition is oxidation and acetate modification. While the hBNP(3-32) fragment was present for all conditions, it makes up on ~0.5-1.0% of the total degradation peak area. Packages sealed without nitrogen purge under vacuum appear to be much more susceptible to oxidation, while pouches sealed under nitrogen show less oxidation. The acetate modifications do not appear to be significantly affected by the packaging conditions. Table 9 summarizes the 1M stability data at 25 C for all packaging configurations tested.

Compared to the control samples (Sample #1), packaged hBNP coated systems in the Tyvek inner pouch with desiccant and nitrogen purge irradiated with 15 kGy e-beam resulted in <3% of hBNP degradation (Sample #2). More degradation was observed in Samples #3 & 4, which were packaged under vacuum without nitrogen purge. At 21 kGy, the % purity is already below the 90% specification. This data indicates that the high oxygen content affects peptide stability upon irradiation. Samples #5-7 show better stability at T=0, particularly for Samples 5 & 7, which both demonstrate extremely low levels of moisture and oxygen.

Following storage for 1M at 2-8 C, systems in packaging configuration #2 irradiated at 15 kGy retained 93.1% total purity with mild total oxidation at 1.4%, which is only 0.8% above non-irradiated controls stored under the same conditions (Sample #1). The acetate/citrate modifications however increased to 2.2% as a result of the e-beam treatment. For the systems packaged under vacuum rather than nitrogen purge (Samples #3&4), both oxidation and acetate/citrate modifications increased above the non-irradiated control values. Systems packaged under vacuum and irradiated at 15 or 21 kGy fell below the 90% total purity threshold following 1M storage at 2-8 C mostly due to the BNP oxidation as a result of the high oxygen head space content.

Systems stored at 25 C exhibited some increase in both oxidation and acetate/citrate modifications due to the elevated storage condition as compared to similarly packaged/irradiated systems stored at 2-8 C. The additional packaging measures of vacuum treating the desiccant, storage without assembly components and storage without Tyvek pouch mitigated the oxidative degradation process but had little affect on the amount of acetate/citrate modification formed during storage at 25 C even for systems maintained in very low humidity and low head space oxygen environment (Sample #7).

Effect of Added Oxygen Absorbers

Additional hBNP (1-32) coated delivery systems were subjected to e-beam treatment in various pouching configurations with and without the addition of an oxygen absorber specifically designed to remove oxygen from the head space of the sealed foil pouch. Table 11 outlines the different packaging configuration for this evaluation.

Systems from each condition were submitted for RP-HPLC purity analysis and head space following e-beam treatment (Table12). All systems that contained an oxygen absorber (02 scrubber) had very high humidity. 02 scrubbers are iron based and can require higher humidity to catalyze the removal of head space 02. For this reason, many 02 scrubber manufacturers include moisture releasing salts with the 02 absorber to maintain a relatively high humidity to allow the iron catalyst to function as intended and remove head space 02. All systems containing the scrubbers achieved lower levels of oxygen compared to control systems.

Following e-beam treatment, samples from each group were analyzed by RP-HPLC purity assay. The results for total hBNP purity are presented in FIG. 13 and the degradation profile for the major degradation products are presented in FIG. 14. The head space analysis is compared against the degradation profile in Table 13. Very low head space moisture (Run #6) or very low head space oxygen (Run #5) prevents degradation by oxidation or acetate modification during e-beam treatment. In addition, the presence of high levels of head space oxygen are not necessarily damaging to the peptide unless there is sufficient level of moisture also in the head space to facilitate the degradation mechanism. Run #7 has very high levels of head space oxygen, however, the extremely dry environment (4% RH) prevents oxidation and or acetate modification of the peptide during e-beam treatment. Run #1 however, with a high level of head space oxygen and a moderate level of moisture (41% RH) shows a dramatic increase in the total oxidation (to 17%) with the level of acetate modifications remaining at lower levels.

Run #4 and Run #9 samples were sealed without desiccant or 02 scrubber, Run #4 with nitrogen purge first, vacuum second and Run #9 with vacuum first then nitrogen. Both conditions performed equivalently with a total purity of ~89% following e-beam treatment. For Run #8 and Run #10, samples were sealed with both 4 A molecular sieve desiccant and 02 scrubber. In Run #8, the pouches were first purged with nitrogen and then vacuum, while pouches in Run #10 were first subjected to vacuum and then purged with nitrogen. Again both sets of samples performed equivalently irrespective of the order of nitrogen purge or vacuum—total purity ~92%.

Fitting the T=0 data from Terminal Sterilization Study #7 and Study #8 into a linear least squares model indicated that hBNP oxidation was sensitive to the level of oxygen (P=0.0047) in the pouch but was not significantly affected by the level of moisture (P=0.9963). In contrast, hBNP degradation by the acetate modification pathways was more affected by moisture (P=0.0002) and not head space oxygen (P=0.7260). Overall, the total BNP purity was affected significantly by moisture (P=0.0004) and less significantly by oxygen (P=0.0623).

Following one month storage at 25 C, samples were analyzed by HPLC. All results reported are averages for n=3 systems packaged under similar conditions. FIG. 15 includes a comparison of the total hBNP purity as determined by RP-HPLC. Data from Run #6 and #7 were generated for Terminal Sterilization Study #7 as sample #2 and #4 respectively. As anticipated from the T=0 stability data, Run #1 through #3 continued to perform poorly with most degradation due to the formation of acetate modifications (FIG. 16) most likely due to the high relatively humidity inside the pouch. Table 14 summarizes the head space analysis and the T=1M 25 C stability data. For packaging conditions that did not reduce the head space oxygen levels (Run #1, 6 and 7), BNP oxidation continued to increase above levels detected at T=0, doubling for these three conditions following one month storage at 25 C. All other packaging conditions, which maintained a low level of head space oxygen (<200 ppm) (Run #2-5 and 8-10), resulted in little to no detectable increase in BNP oxidation following one month at 25 C. Therefore while not evident at T=0 (e.g. Run #6 and 7), high levels of head space oxygen will lead to an increased rate of BNP oxidation during storage. Therefore, maintaining low levels of oxygen in the pouch is beneficial.

With the exception of Run #1 packaging configurations which contained high levels of head space moisture contained high levels of acetate modifications. Samples packaged under the negative control conditions were severely degraded after one month storage at 25 C, with a total purity of only 42%. Acetate modifications into other degradation species can result from advanced degradation/further decomposition.

Figure 17:
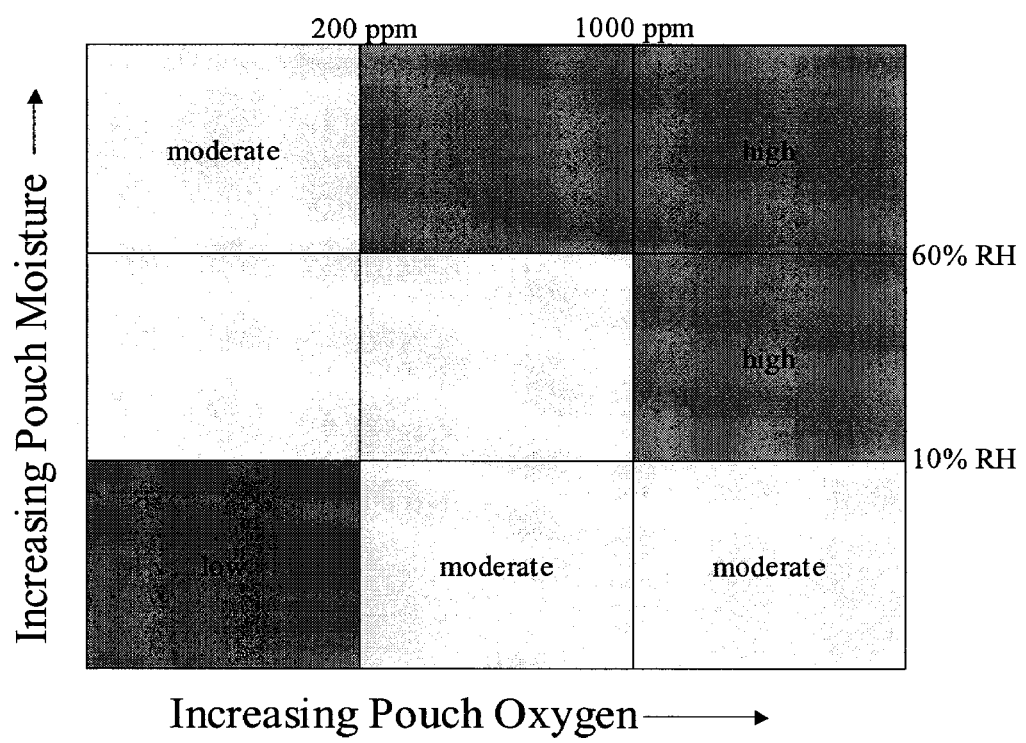
FIG. 17 is a diagram illustrating factors affecting hBNP Oxidation.
Figure 18:
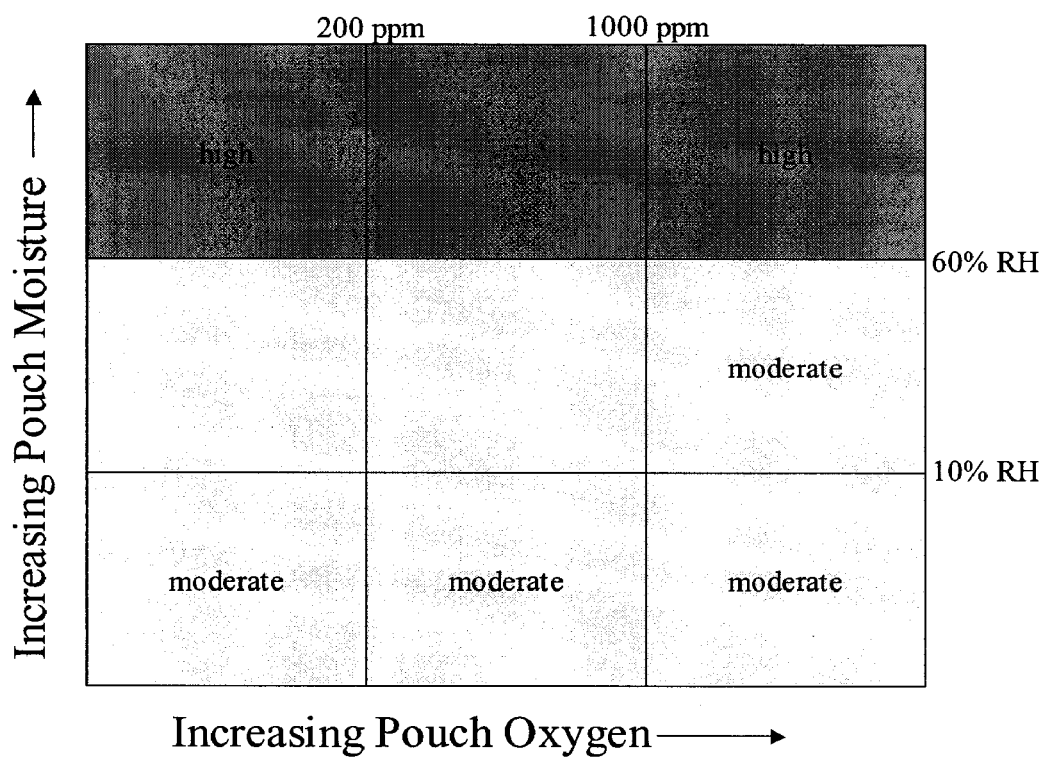
FIG. 18 is a diagram illustrating factors affecting hBNP acetate modifications.

The above data confirm that the condition of the pouch environment, in terms of moisture and oxygen is an important contributor to BNP degradation following e-beam treatment. FIGS. 17 and 18 attempt to summarize the cause and effect relationship illustrated by the experiments. If oxygen and moisture levels inside the pouch are high (>60% RH and 1000 ppm 02), BNP will degrade readily to form oxidized BNP and acetate modifications during e-beam treatment. Minimizing both moisture and oxygen in the pouch reduces BNP degradation by both mechanisms. However, both mechanisms are more sensitive to moisture levels, which should be rigorously maintained at low levels to preserve peptide stability.

TABLE 5

Packing Conditions Matrix

| Group | Packaging Conditions | Irradiation Conditions | T = 0 | Temp | Total | 1 M | 3 M | 6 M | 9/12 M |
|---|---|---|---|---|---|---|---|---|---|
| A | Sealed foil pouch with Tyvek inner pouch, Nitrogen Purge | None (shipping controls) | ✓ | −20° C. | ✓ | ✓ | — | — | — |
| | | | | 2-8° C. | ✓ | ✓ | ✓ | ✓ | ✓ |
| | | | | 25° C. | ✓ | ✓ | ✓ | ✓ | ✓ |
| | | | | 40° C. | ✓ | ✓ | — | — | — |
| | | 15 kGy/ambient temperature | ✓ | −20° C. | ✓ | ✓ | — | — | — |
| | | | | 2-8° C. | ✓ | ✓ | ✓ | ✓ | ✓ |
| | | | | 25° C. | ✓ | ✓ | ✓ | ✓ | ✓ |
| | | 21 kGy/ambient temperature | ✓ | −20° C. | ✓ | ✓ | — | — | — |
| | | | | 2-8° C. | ✓ | ✓ | ✓ | ✓ | ✓ |
| | | | | 25° C. | ✓ | ✓ | ✓ | ✓ | ✓ |
| B | Foil and Tyvek, Sealed under vacuum without | 15 kGy/ambient temperature | ✓ | 2-8° C. | ✓ | ✓ | ✓ | ✓ | ✓ |
| | | | | 25° C. | ✓ | ✓ | ✓ | ✓ | ✓ |
| | | 21 kGy/ambient temperature | ✓ | 2-8° C. | ✓ | ✓ | ✓ | ✓ | ✓ |
| | | | | 25° C. | ✓ | ✓ | ✓ | ✓ | ✓ |

TABLE 5-continued

Packing Conditions Matrix

| Group | Packaging Conditions | Irradiation Conditions | T = 0 | Temp | Total | 1 M | 3 M | 6 M | 9/12 M |
|---|---|---|---|---|---|---|---|---|---|
| C | Vac. Desiccant | 21 kGy/ambient temperature | ✓ | 25° C. | ✓ | ✓ | — | — | — |
| D | Array Only (w/o desicc.) | | | | ✓ | ✓ | — | — | — |
| E | Array and Tyvek Only (no desicc.) | | ✓ | | ✓ | ✓ | — | — | — |

TABLE 6

Stability Protocol

| Group | Tyvek pouch | '+' = Nitrogen Purge/ '−' = Vacuum | Assembly Components. | Vacuum Drying of Desiccant | Desiccant | Foil Pouch |
|---|---|---|---|---|---|---|
| A | + | + | + | − | + | + |
| B | + | − | + | − | + | + |
| C | + | + | + | + | + | + |
| D | − | + | − | − | − | + |
| E | + | + | − | − | + | + |

TABLE 7

Summary of Head Space Analysis

| Sample Number | | 1 | 1(repeat) | 1(repeat) | 2 | 3 | 4 | 5 | 6 | 7 |
|---|---|---|---|---|---|---|---|---|---|---|
| NITROGEN | ppm | 994062 | 994254 | 994242 | 995935 | 853524 | 828976 | 995220 | 997884 | 997064 |
| OXYGEN | ppm | 5178 | 5039 | 5088 | 753 | 111750 | 148190 | ND | ND | ND |
| ARGON | ppm | 402 | 393 | 396 | 458 | 9389 | 9199 | 425 | 106 | 190 |
| CO2 | ppm | 187 | 172 | 155 | 205 | 364 | 223 | 144 | 652 | 175 |
| MOISTURE | ppm | 49 | 29 | 18 | 104 | 226 | 234 | 31 | 745 | 16 |
| HYDROGEN | ppm | 122 | 113 | 101 | 2545 | 24747 | 13178 | 4180 | 613 | 2555 |
| R.H. (@25 C., 760 torr) | % | 0 | 0 | 0 | 0 | 1 | 1 | 0 | 3 | 0 |
| R.H. (@5 C., 760 torr) | % | 1 | 1 | 0 | 2 | 4 | 4 | 1 | 11 | 0 |
| Packaging Type | | A | A | A | A | B | B | C | D | E |
| E-beam Treatment | | NA | NA | NA | 15 kGy | 15 kGy | 21 kGy | 21 kGy | 21 kGy | 21 kGy |
| Packaged with Desiccant | | + | + | + | + | + | + | + | − | + |
| + = Nitrogen/− = Vacuum | | + | + | + | + | − | − | + | + | + |
| Vac/N2 treated desiccant | | − | − | − | − | − | − | + | − | − |
| Inner Tyvek Pouch | | + | + | + | + | + | + | + | − | + |
| Assembly Components | | + | + | + | + | + | + | + | − | − |

TABLE 8

Data Summary

| Sample # | N2 Purge | Vacuum | Desiccant | O2 Scrubber | Comments | Head Space Moisture (% RH) | Head Space Oxygen (ppm) | E-beam Conditions (room temp) | hBNP Purity (%) | Total Oxidation (%) | Acetate/ Citrate modification, RRT > 1.33 (%) |
|---|---|---|---|---|---|---|---|---|---|---|---|
| 1 | + | − | + | − | shipping control | 0 | 5102 | None | 96.4 | 0.5 | 0.1 |
| 2 | + | − | + | − | | 2 | 753 | 15 kGy | 93.7 | 1.3 | 1.7 |
| 3 | − | + | + | − | | 4 | 111750 | 15 kGy | 91.2 | 2.9 | 2.2 |
| 4 | − | + | + | − | | 4 | 148100 | 21 kGy | 89.6 | 3.1 | 3.2 |
| 5 | + | − | + | − | Treated desiccant | 1 | 0 | 21 kGy | 92.8 | 1.7 | 2.1 |
| 6 | + | − | − | − | No assembly components or desiccant | 11 | 0 | 21 kGy | 91.3 | 2.2 | 1.8 |
| 7 | + | − | + | − | No Tyvek pouch or assembly components | 0 | 0 | 21 kGy | 93.0 | 1.3 | 2.0 |

TABLE 9

One month 25 C. Stability Data Summary.

| Sample # | N₂ Purge | Vacuum | Desiccant | O₂ Scrubber | Comments | Head Space Moisture (% RH) | Head Space Oxygen (ppm) | E-beam Conditions (room temp) | 1 M, 25 C. hBNP Purity (%) | 1 M 25 C., Total Oxidation (%) | 1 M, 25 C. Acetate modification |
|---|---|---|---|---|---|---|---|---|---|---|---|
| 1 | + | − | + | − | shipping control | 1 | 5102 | None | 96.6 | 0.6 | 0.2 |
| 2 | + | − | + | − | | 2 | 753 | 15 kGy | 91.5 | 2.3 | 2.6 |
| 3 | − | + | + | − | | 4 | 111750 | 15 kGy | 85.7 | 6.8 | 3.0 |
| 4 | − | + | + | − | | 4 | 148190 | 21 kGy | 83.6 | 7.5 | 3.6 |
| 5 | + | − | + | − | Treated desiccant | 1 | 0 | 21 kGy | 90.5 | 2.4 | 3.2 |
| 6 | + | − | − | − | No assembly components or desiccant | 11 | 0 | 21 kGy | 91.4 | 1.6 | 2.9 |
| 7 | + | − | + | − | No Tyvek pouch or assembly components | 0 | 0 | 21 kGy | 91.6 | 1.3 | 3.2 |

TABLE 10

One Month 2-8 C. Stability Data Summary

| Sample # | N₂ Purge | Vacuum | Desiccant | O₂ Scrubber | Comments | Head Space Moisture (% RH) | Head Space Oxygen (ppm) | E-beam Conditions (room temp) | 1 M, 2-8 C. hBNP Purity (%) | 1 M 2-8 C., Total Oxidation (%) | 1 M, 2-8 C. Acetate modification |
|---|---|---|---|---|---|---|---|---|---|---|---|
| 1 | + | − | + | − | shipping control | 1 | 5102 | None | 96.9 | 0.8 | 0.0 |
| 2 | + | − | + | − | | 2 | 753 | 15 kGy | 93.1 | 1.4 | 2.2 |
| 3 | − | + | + | − | | 4 | 111750 | 15 kGy | 88.8 | 4.7 | 2.3 |
| 4 | − | + | + | − | | 4 | 148190 | 21 kGy | 87.0 | 4.7 | 3.7 |

TABLE 11

Packaging Study Design

| Run | Nitrogen | Vacuum | Desiccant | O2 Scrubber | Comments |
|---|---|---|---|---|---|
| 1 | − | − | − | − | N/A |
| 2 | + | − | − | + | N/A |
| 3 | − | + | − | + | N/A |
| 4 | + | + | − | − | Nitrogen 1$^{st}$, Vacuum 2$^{nd}$ |
| 5 | − | − | + | + | N/A |
| 6 | + | − | + | − | Previous study |
| 7 | − | + | + | − | Previous study |
| 8 | + | + | + | + | Nitrogen 1$^{st}$, Vacuum 2$^{nd}$ |
| 9 | + | + | − | − | Vacuum 1$^{st}$, Nitrogen 2$^{nd}$ |
| 10 | + | + | + | + | Vacuum 1$^{st}$, Nitrogen 2$^{nd}$ |

TABLE 12

Head Space Analysis

| SAMPLE ID | | Run #1 | Run #2 | Run #3 | Run #4 | Run #5 | Run #6 | Run #7 | Run #8 | Run #9 | Run #10 |
|---|---|---|---|---|---|---|---|---|---|---|---|
| NITROGEN | ppm | 787961 | 973502 | 904959 | 923021 | 969566 | 995935 | 828976 | 957206 | 994988 | 982434 |
| OXYGEN | ppm | 187385 | 170 | 189 | 172 | ND | 753 | 148190 | 130 | 149 | 132 |
| ARGON | ppm | 9478 | 615 | 10725 | 3824 | 10784 | 458 | 9199 | 2603 | 223 | 291 |
| CO2 | ppm | 5420 | 151 | 158 | 14243 | 159 | 205 | 223 | 613 | 1344 | 609 |
| MOISTURE | ppm | 3336 | 21906 | 25126 | 2881 | 11509 | 104 | 234 | 12732 | 1318 | 13026 |
| HYDROGEN | ppm | 6430 | 3656 | 58843 | 55859 | 7960 | 2545 | 13178 | 26716 | 1978 | 3508 |
| R.H. (@25 C., 760 torr) | % | 11 | 58 | 78 | 9 | 36 | 0 | 1 | 40 | 5 | 37 |
| R.H. (@5 C., 760 torr) | % | 41 | 100 | 100 | 36 | 100 | 2 | 4 | 100 | 15 | 100 |
| Packaging Conditions | | | | | | | | | | | |
| Irradiation | | 21 kGy/ RT | 21 kGy/ RT | 21 kGy/ RT | 21 kGy/ RT | 21 kGy/ RT | 21 kGy/ RT | 21 kGy/ RT | 21 kGy/ RT | 21 kGy/ RT | 21 kGy/ RT |
| N2 Purge | | − | + | − | + | − | + | − | + | + | + |
| Vacuum | | − | − | + | + | − | − | + | + | + | + |
| Desiccant | | − | − | − | − | + | + | + | + | − | + |

TABLE 12-continued

Head Space Analysis

| SAMPLE ID | Run #1 | Run #2 | Run #3 | Run #4 | Run #5 | Run #6 | Run #7 | Run #8 | Run #9 | Run #10 |
|---|---|---|---|---|---|---|---|---|---|---|
| O2 Scrubber | − | + | + | − | + | − | − | + | − | + |
| Comments | Negative Control | | | Nitrogen first vacuum second | | From TS #7 | From TS #7 | Nitrogen first vacuum second | Vacuum first Nitrogen second | Vacuum first Nitrogen second |

TABLE 13

Comparison between head space and T = 0 stability data

| Sample # | $N_2$ Purge | Vacuum | Desic-cant | $O_2$ Scrubber | Comments | Head Space Moisture (% RH) | Head Space Oxygen (ppm) | E-Beam Conditions (RT) | hBNP Purity (%) | Total Oxidation (%) | Acetate/Citrate modification, RRT > 1.33 (%) |
|---|---|---|---|---|---|---|---|---|---|---|---|
| Run #1 | − | − | − | − | Negative Control | 41 | 187365 | 21 kGy | 75.0 | 17.3 | 2.0 |
| Run #2 | + | − | − | + | | 100 | 170 | 21 kGy | 59.3 | 2.4 | 35.8 |
| Run #3 | − | + | − | + | | 100 | 189 | 21 kGy | 53.1 | 0.7 | 33.8 |
| Run #4 | + | + | − | − | Nitrogen first vacuum second | 35 | 172 | 21 kGy | 59.5 | 4.8 | 2.0 |
| Run #5 | − | − | + | + | | 100 | ND | 21 kGy | 92.4 | 1.2 | 2.5 |
| Run #6 | + | − | + | − | From TS #7 | 2 | 753 | 15 kGy | 95.7 | 1.3 | 1.7 |
| Run #7 | − | + | + | − | From TS #7 | 4 | 148190 | 21 kGy | 89.6 | 3.1 | 3.2 |
| Run #8 | + | + | + | + | Nitrogen first vacuum second | 100 | 130 | 21 kGy | 91.7 | 1.0 | 3.6 |
| Run #9 | + | + | − | − | Vacuum first Nitrogen second | 12 | 149 | 21 kGy | 88.8 | 4.5 | 2.7 |
| Run #10 | + | + | + | + | Vacuum first Nitrogen second | 100 | 132 | 21 kGy | 92.3 | 1.1 | 2.8 |

TABLE 14

Comparison between headspace data and T = 1 M, 25 C. stability data

| Sample # | N2 Purge | Vacuum | Desic-cant | 02 Scrubber | Comments | Head Space Moisture (ARH) | Head Space Oxygen | E-Beam Conditions (RT) | M, 25 C. hBNP Purity (%) | 1 M 25 C., Total Oxidation (%) | 1 M, 25 C. Acetate modifica-tion |
|---|---|---|---|---|---|---|---|---|---|---|---|
| Run #1 | − | − | − | − | Negative Control | 41 | 187385 | 21 kGy | 42.18 | 37.10 | 2.59 |
| Run #2 | + | − | − | + | | 100 | 170 | 21 kGy | 34.06 | 0.51 | 52.93 |
| Run #3 | − | + | − | + | | 100 | 189 | 21 kGy | 30.71 | 0.46 | 39.67 |
| Run #4 | + | + | − | − | Nitrogen first vacuum second | 36 | 172 | 21 kGy | 88.47 | 3.45 | 3.48 |
| Run #5 | − | − | + | + | | 100 | ND | 21 kGy | 90.54 | 1.27 | 4.05 |
| Run #6 | + | − | + | − | From TS #7 | 2 | 753 | 15 kGy | 91.49 | 2.31 | 2.56 |
| Run #7 | − | + | + | − | From TS #7 | 4 | 148190 | 21 kGy | 83.63 | 7.53 | 3.64 |
| Run #8 | + | + | + | + | Nitrogen first vacuum second | 100 | 130 | 21 kGy | 90.15 | 1.38 | 4.48 |
| Run #9 | + | + | − | − | Vacuum first Nitrogen second | 12 | 149 | 21 kGy | 88.76 | 3.65 | 3.67 |
| Run #10 | + | + | + | + | Vacuum first Nitrogen second | 100 | 132 | 21 kGy | 87.79 | 1.14 | 7.22 |

The invention claimed is:

1. A method for manufacturing a transdermal delivery device, wherein said transdermal delivery device comprises a microprojection member comprising a coated array, an adhesive backing and a retainer ring; wherein the method comprises the following steps: (i) providing a microprojection member having a plurality of microprojections, an adhesive backing and a retainer ring; (ii) providing a biocompatible coating formulation comprising a biologically active agent, wherein the biologically active agent comprises a biological agent selected from the group consisting of: Glucagon and HGH; (iii) coating the microprojection member with the biocompatible coating formulation to form said transdermal delivery device; and (iv) packaging said transdermal delivery device by heat sealing said transdermal delivery device in a foil pouch or foil cup containing a desiccant and purged with dry nitrogen gas to form an inert dry atmosphere, wherein the step of coating further comprises depositing the biocompatible coating formulation in the range of 10 to 200 picoliters per microprojection or 0.1 to 20 nanoliters per microprojection.

2. The method of claim 1, wherein the desiccant is a molecular sieve desiccant comprising calcium oxide, clay desiccant, calcium sulfate, silica gel or a mixture thereof.

3. The method of claim 1, wherein the inert atmosphere comprises carbon dioxide.

4. The method of claim 1, wherein the inert atmosphere comprises argon, helium, neon, krypton, or a mixture thereof.

5. The method of claim 1, wherein the inert atmosphere has essentially zero water content.

6. The method of claim 1, further comprising providing a purge device to reduce moisture or oxygen content during packaging.

7. The method of claim 1, wherein packaging said transdermal delivery device is carried out under partial vacuum.

8. The method of claim 1, wherein packaging comprises providing a foil-lined chamber.

9. The method of claim 8, wherein said transdermal delivery device is enclosed in said foil-lined chamber.

10. The method of claim 8, wherein the chamber comprises a foil lid, and a desiccant and/or oxygen absorber is attached to the foil lid wherein said chamber is sealed by the foil lid.

11. The method of claim 10, wherein the chamber is purged with nitrogen prior to sealing the chamber.

* * * * *